US010869831B2

(12) United States Patent
Megiddo

(10) Patent No.: US 10,869,831 B2
(45) Date of Patent: *Dec. 22, 2020

(54) TREATMENT OF PROTEIN AGGREGATION MYOPATHIC AND NEURODEGENERATIVE DISEASES BY PARENTERAL ADMINISTRATION OF TREHALOSE

(71) Applicant: Seelos Therapeutics, Inc., New York, NY (US)

(72) Inventor: Dalia Megiddo, Nataf (IL)

(73) Assignee: Seelos Therapeutics, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/460,046

(22) Filed: Jul. 2, 2019

(65) Prior Publication Data

US 2019/0374463 A1   Dec. 12, 2019

Related U.S. Application Data

(63) Continuation of application No. 14/889,727, filed as application No. PCT/IL2014/050411 on May 7, 2014, now Pat. No. 10,493,023.

(60) Provisional application No. 61/820,278, filed on May 7, 2013.

(51) Int. Cl.
A61K 31/7016 (2006.01)
A61K 9/00 (2006.01)
A61K 9/08 (2006.01)

(52) U.S. Cl.
CPC ............ A61K 9/0019 (2013.01); A61K 9/08 (2013.01); A61K 31/7016 (2013.01)

(58) Field of Classification Search
None
See application file for complete search history.

(56) References Cited

U.S. PATENT DOCUMENTS

| | | |
|---|---|---|
| 6,440,446 B1 | 8/2002 | Yoshizane |
| 6,555,526 B2 | 4/2003 | Matsuo |
| 6,602,865 B1 | 8/2003 | Andrasi |
| 7,214,667 B2 | 5/2007 | Fukuda |
| 7,732,425 B2 | 6/2010 | Matsuo |
| 7,854,922 B2 | 12/2010 | Tanabe |
| 7,956,181 B2 | 6/2011 | Ehara |
| 8,163,713 B2 | 4/2012 | Nishizawa |
| 8,283,337 B2 | 10/2012 | Sasaki |
| 8,741,871 B2 | 6/2014 | Nishizawa |
| 8,889,651 B2 | 11/2014 | Liu |
| 9,084,720 B2 | 7/2015 | Megiddo |
| 9,125,924 B2 | 9/2015 | Megiddo |
| 9,155,751 B2 | 10/2015 | Suzuki |
| 9,186,356 B2 | 11/2015 | Shen |
| 9,572,825 B2 | 2/2017 | Megiddo |
| 2005/0215562 A1 | 9/2005 | Tremblay |
| 2009/0110671 A1 | 4/2009 | Miyata |
| 2009/0110746 A1 | 4/2009 | Gainer |
| 2010/0035837 A1 | 2/2010 | Sasaki |
| 2010/0093993 A1 | 4/2010 | Nishizawa |
| 2011/0224423 A1 | 9/2011 | Chung |
| 2013/0310467 A1 | 11/2013 | Morkiaku |
| 2013/0316971 A1 | 11/2013 | Yang |
| 2014/0066439 A1 | 3/2014 | Gunst |
| 2014/0336145 A1 | 11/2014 | Megiddo |
| 2015/0025028 A1 | 1/2015 | Lee-Chen |
| 2015/0025035 A1 | 1/2015 | Chung |
| 2015/0118196 A1 | 4/2015 | Wada |
| 2015/0196575 A1 | 7/2015 | Megiddo |
| 2016/0022716 A1 | 1/2016 | Megiddo |
| 2016/0101122 A1 | 4/2016 | Megiddo |
| 2016/0120798 A1 | 5/2016 | Megiddo |
| 2016/0303150 A1 | 10/2016 | Megiddo |
| 2017/0020905 A1 | 1/2017 | Megiddo |

FOREIGN PATENT DOCUMENTS

| | | |
|---|---|---|
| EP | 1354590 | 10/2003 |
| JP | 4033510 | 9/1997 |
| JP | 3455633 | 1/1998 |
| JP | 2001302517 | 10/2001 |
| JP | 2006342108 | 12/2006 |
| JP | 2007510758 | 4/2007 |
| JP | 4950521 | 9/2007 |
| JP | 2008545628 | 12/2008 |
| JP | 4255101 | 4/2009 |
| JP | 2009517086 | 4/2009 |
| JP | 2012524035 | 10/2012 |
| JP | 5106109 | 12/2012 |
| JP | 2013006773 | 1/2013 |
| JP | 2014139160 | 7/2014 |
| JP | 2014227404 | 12/2014 |
| WO | WO 1997024129 | 7/1997 |
| WO | WO 2005046360 | 5/2005 |
| WO | WO 2006124892 | 11/2006 |
| WO | WO 2008014685 | 2/2008 |
| WO | WO 2008133884 | 11/2008 |
| WO | WO 2010008860 | 1/2010 |
| WO | WO 2010118888 | 10/2010 |
| WO | WO 2014018133 | 1/2014 |

OTHER PUBLICATIONS

Kruger, et al., "Autophagic degradation of tau in primary neurons and its enhancement by trehalose," Neurobiology of Aging, 2012, 33:2291-2305.
Amyotrophic Lateral Sclerosis (ALS) Fact Sheet published 2013 by the National Institute of Neurological Disorders and Stroike, downloaded from www.ninds.nih.gov.
Anonymous, "Trehalose in oculopharyngeal muscular dystrophy: The HOPEMD; NCT02015481 study", Integrity, Thomson-Pharma, Dec. 20, 2013.
Bachmanov et al., "Food Intake, Water Intake, and Drinking Spout Side Preference of 28 Mouse Strains." Behav Genet (2002) vol. 32 No. 6 pp. 435-443.
Beal, M. F. (2010). Parkinson's disease: a model dilemma Nature, S8.

(Continued)

Primary Examiner — Dale R Miller
(74) Attorney, Agent, or Firm — Fish & Richardson P.C.

(57) ABSTRACT

Disclosed is a method of treatment of a disease associated with abnormal protein aggregation comprising parenterally administering pharmaceutical formulations comprising trehalose. Also disclosed is an injectable aqueous pharmaceutical formulation comprising a therapeutically effective amount of trehalose.

14 Claims, 2 Drawing Sheets

(56) References Cited

OTHER PUBLICATIONS

Becher et al., "Oculopharyngeal muscular dystrophy in Hispanic New Mexicans.", JAMA. 286(19): 2437-40, 2001.
Becker, L.C. et al. Final Report of the Safety assessment of Hyaluronic Acid, Potassium Hyaluronate, and Sodium Hyaluronate, (2009) International J. of Toxicology, vol. 28 pp. 5-67.
Berg et al., "Correlation between morphological alterations and enzyme activities in the mucosa of the small intestine.", Scand J Gastroenterol 8: 703-712, 1973.
Blumen et al., "Epidemiology and inheritance of oculopharyngeal muscular dystrophy in Israel", Neuromuscul Disord 7: S38-40, 1997.
Brunet et al., "Dystrophie musculaire oculo-pharyngee. Recensement des familles frarnaises et etudes genealogiques.", Rev Neurol 4: 429-434, 1990.
Buteau, "Deuterated Drugs: Unexpectedly Nonobvious?", Journal of High Technology Law 22, 53 pages, 2009.
Crook, Z. and Houseman, D. Huntington's disease: can mice lead the way to treatment? (2011) Neuron, vol. 69 pp. 423-435 (epubdoi:10.1016/j.neuron.2010.12.035, pp. 1-25.
Davies et al "Trehalose reduces aggregate formation and delays pathology in a transgenic mouse model of oculopharyngeal muscular dystrophy", Human Molecular Genetics, vol. 15, No. 1, Nov. 30, 2005, pp. 23-31.
Davies et al., "Oculopharyngeal muscular dystrophy: Potential therapies for an aggregate-associated disorder", International Journal of Biochemistry and Cell Biology, Pergamon, GB, vol. 38, No. 9, Jan. 1, 2006, pp. 1457-1462.
De Buck, S. et al. Prediction of human pharmacokinetics using physiologically based modeling: a retrospective analysis of 26 clinically tested drugs. (2007) Drug Metabolism and Disposition, vol. 35, pp. 1766-1780.
Dickson, "Neuropathology of non-Alzheimer degenerative disorders" Int J Clin Exp Pathol (2010) vol. 3 No. 1 pp. 1-23.
Duty, S. and Jenner, P. Animal models of Parkinson's disease: a source of novel treatments and clues to the cause of the disease. (2011) British Journal of Pharmacology. vol. 164, pp. 1357-1391.
Emea, "Avastin: EPAR-European Medicines Agency", Jan. 1, 2005, pp. 1-61.
Goodman, "Neuroinflammation (Part 2): Another Role for Trehalose?", Huntington's Disease Drug Works, Nov. 30, 2008, 3 pages.
Grewal et al., "Mutation Analysis of Oculopharyngeal Muscular Dystrophy in Hispanic American Families", Arch Neurol 56(11): 1378-1381, 1999.
Hopkins, U. and Arias, C.Y. Large-volume IM injections: a Review of Best Practices (Feb. 2013) Oncoloqv Nurse Advisor, pp. 32-37.
Hore et al., "Studies on disaccharidase activities of the small intestine of the domestic cat and other carnivorous mammals.", Comp Biochem Pbysiol 24: 717-725, 1968.
International Conference on Harmonisation of Technical Requirements for Registration of Pharmaceuticals for Human Use. "Impurities: Guideline for Residual Solvents Q3C(R5)" Feb. 4, 2011.
International Search Report for the International Application No. PCT/IL2014/050411, dated Sep. 22, 2014.
Lange, "Current research on the neuroprotective therapy of Huntington's Disease", Materialien zur Huntington-Krankheit, Nr. 180, Jun. 1, 2008, pp. 1-12.
Langer, "New methods of drug delivery.", Science 28; 249: 1527-1533, 1990.
Li et al., "The Use of the R6 Transgenic Mouse Models of Huntington's Disease in Attempts to Develop Novel Therapeutic Strategies", The Journal of the American Society for Experimental NeuroTherapeutics 2: 447-464, 2005.

Luyckx and Baudouin "Trehalose: an intriguing disaccharide with potential for medical application in ophthalmology", Clinical Ophthalmology, May 1, 2011, pp. 577-581.
March "Advanced Organic Chemistry: Reactions, Mechanisms and Structure", 4th Ed., New York: Wiley-lnterscience, 1992.
McClellan et al., "Molecular chaperones and the art of recognizing a lost cause.", Nat Cell Biol 3: E51-E53, 2001.
Meyer-Luehmann et al., "Rapid appearance and local toxicity of amyloid-β plaques in a mouse model of Alzheimer's disease", Nature 451: 720-724, 2008.
Australian Office Action in Application No. 2014264228, dated Jun. 24, 2019, 10 pages.
Oral Trehalose Therapy to Reverse Arterial Aging in Middle-Aged and Older Adults. http://clinicaltrials.gov/ct2/show/NCT01575288, 2015.
Perucho et al., "Trehalose Protects from Aggravation of Amyloid Pathology Induced by Isoflurane Anesthesia in APPswe Mutant Mice" Current Alzheimer's Research, vol. 9, pp. 334-343, 2012.
Rodríguez-Navarro et al. "Trehalose ameliorates dopaminergic and tau pathology in parkin deleted/tau overexpressing mice through autophagy activation", Neurobiology of Disease, vol. 39, pp. 423-438, 2010.
Rowe et al Handbook of Phannaceutical Excipients, McGraw Hill, 7 pages, 2006.
Seidel et al., "Brain pathology of spinocerebellar ataxias." Acta Neuropathol (2012) vol. 124 pp. 1-21.
Seki et al, "Effect of Trehalose on the Properties of Mutant γPKC, Which Causes Spinocerebellar Ataxia Type 14, in Neuronal Cell lines and Cultured Purkinje Cells." The Journal of Biological Chemistry vol. 285, No. 43, pp. 33252-33264, Oct. 22, 2010.
Shatsky, M. Evidence for the Use of Intramuscular Injection in Outpatient Practice. (2009) American Family Physician, vol. 79 (4), oo. 297-300.
Shepherd et al., Short-Chain Carbohydrates and Functional Gastrointestinal Disorders American Journal of Gastroenterology (2013) vol. 108 pp. 707-717.
Spires-Jones et al., "Passive immunotherapy rapidly increases structural plasticity in a mouse model of Alzheimer disease", Neurobiol Dis 33: 213-220, 2009.
Stephan, A., & Phillips, A. G. (2005). A case for a non-transgenic animal model of Alzheimer's disease. Genes, Brain and Behavior, 4(3), 157-172.
Tanaka et al., "A novel therapeutic strategy for polyglutamine diseases by stabilizing aggregationprone proteins with small Molecules." J Mo/ Med (2005) vol. 83 pp. 343-352.
Tanaka et al., "Trehalose alleviates polyglutamine-mediated pathology in a mouse model of Huntington disease", Nature Medicine, vol. 10, No. 2, Jan. 18, 2004, pp. 148-154.
Vonsattel, J. P. G. (2008). Huntington disease models and human neuropathology: similarities and differences. Acta neuropathologica, 115(1 ), 55-69.
Trehalose, "WHO Food Additives", (httplAvww.inchem.orgldocuments/jecfa/jecmono1v46je05.htm), Jul. 2, 2019, 15 pages.
Winklhofer et al., "Geldanamycin Restores a Defective Heat Shock Response in Vivo", J Biol Chem 276: 45160-45167, 2001.
Wirths, A. nd Bayer, T. Neuron loss in transgenic mouse models of Alzheimer's disease. (2010) International Journal of Alzheimer's Disease, doi:10.4061/2010/723782 (pp. 1-6 provided).
European Medicines Agency, "ICH guideline Q3C (R5) on impurities: guideline for residual solvents", World wide web (www) tga.gov.au/pdf/euguide/ich822602006.pclf, Aug. 2011.
Yamamoto et al., "Reversal of Neuropathology and Motor Dysfunction in a Conditional Model of Huntington's Disease.", Cell 101: 57-66, 2000.
Yang and Yu "lntracerebral Transplantation of Neural Stem Cells Combined With Trehalose Ingestion Alleviates Pathology in a Mouse Model of Huntington's Disease", Journal of Neuroscience Research 87:26-33 (2009).
Office Action in JP Appln. No. 2019-075517, dated May 12, 2020, 12 pages (with English translation).

TREATMENT OF PROTEIN AGGREGATION MYOPATHIC AND NEURODEGENERATIVE DISEASES BY PARENTERAL ADMINISTRATION OF TREHALOSE

This application is a continuation of U.S. patent application Ser. No. 14/889,727, filed on Nov. 6, 2015, which is a National Stage Entry of PCT Application No. PCT/IL2014/050411, filed on May 7, 2014, which claims the benefit of priority to U.S. Provisional Application No. 61/820,278, filed on May 7, 2013.

TECHNOLOGICAL FIELD

The presently disclosed subject matter relates to use of trehalose in the treatment of myopathies, neurodegenerative disorders or tauopathies associated abnormal protein aggregation.

BACKGROUND ART

References considered to be relevant as background to the presently disclosed subject matter are listed below:
[1] Brunet, G. et al., 1990 Dystrophie musculaire oculopharyngée. Recensement des familes françaises et études généalogiques. Rev Neurol 4:429-434.
[2] Blumen, S. C. et al., 1997 Epidemiology and inheritance of oculopharyngeal muscular dystrophy in Israel. Neuromuscul Disord 7:S38-40.
[3] Becher, M. W. et al., 2001 Occulopharyngeal Muscular Dystrophy in Hispanics New Mexicans. JAMA. 286(19):2437-40.
[4] Grewal, R. J. et al., 1999 Mutation Analysis of Oculopharyngeal Muscular Dystrophy in Hispanic American Families. Arch Neurol 56(11):1378-1381.
[5] Yamamoto, A. et al., 2000. Reversal of neuropathology and motor dysfunction in a conditional model of Huntington's disease. Cell 101:57-66.
[6] J Meyer-Luehmann, M. et al., 2008. Rapid appearance and local toxicity of amyloid-beta plaques in a mouse model of Alzheimer's disease. Nature 451:720-724.
[7] Spires-Jones, T. L. et al., 2009. Passive immunotherapy rapidly increases structural plasticity in a mouse model of Alzheimer disease. Neurobiol Dis 33:213-220.
[8] McClellan, A. J. & Frydman, 2001. Molecular chaperones and the art of recognizing a lost cause. Nat Cell Biol 3:E51-E53.
[9] Winklhofer, K. F. et al., 2001. Geldanamycin restores a defective heat shock response in vivo. J Biol Chem 276:45160-45167.
[10] Tanaka, M. et al., 2004. Trehalose alleviates polyglutamine-mediated pathology in a mouse model of Huntington disease. Nat Med 10:148-154.
[11] Davies; J. E. et al., 2006. Trehalose reduces aggregate formation and delays pathology in a transgenic mouse model of oculopharengeal muscular dystrophy. Hum Mol Genet 15:23-31.
[12] WHO Food Additives (http://www.inchem.org/documents/jecfa/jecmono/v46je05.htm).
[13] Berg, N. O. et al., 1963. Correlation between morphological alterations and enzyme activities in the mucosa of the small intestine. Scand Gastroenterol 8:703-712.
[14] Hore, P. & Messer, M. 1968. Studies on disaccharidase activities in the small intestine of domestic cats and other carnivorous mammals. Comp Biochem Physiol 24:717-725.
[15] http://www.tga.gov.au/pdf/euguide/ich822602006.pdf.
[16] Langer R 1990. New methods of drug delivery. Science 28; 249:1527-1533.
[17] Oral Trehalose Therapy to Reverse Arterial Aging in Middle-Aged and Older Adults. http://clinicaltrials.gov/ct2/show/NCT01575288.

Acknowledgement of the above references herein is not to be inferred as meaning that these are, in any way relevant to the patentability of the presently disclosed subject matter.

BACKGROUND

Several groups of diseases resulting from trinucleotide repeat mutations are known. These diseases are characterized by abnormal stretches of amino acids in specific proteins encoded by a mutated gene. The mutant protein aggregates in cells causing typical citotoxic cellular inclusion bodies.

Disorders identified as protein codon reiteration disorders contain expansions of a homopolymeric stretch of amino acids, specifically polyglutamine (poly Q) or polyalanine (poly A). At least eight neurodegenerative disorders have been associated with polyglutamine expansions, including Huntington's disease (HD), spinal and bulbar muscular atrophy (SBMA), dentatortibral and pallidoluysian atrophy (DRPLA), and several forms of spinocerebellar ataxia (SCA). Polyalanine expansions are associated with several rare and severe congenital abnormalities, but also with oculopharyngeal muscular dystrophy (OPMD). Additional conditions associated with polyalanine expansions expansion may include dystrophic disorders.

One such disease is Oculopharyngeal Muscular Dystrophy (OPMD), a rare inherited myopathy characterized by ptosis, severe dysphagia and proximal limb weakness. Its estimated prevalence is 1:100,000 and the largest clusters reported were in families of French-Canadians origin in Canada and in the US (prevalence 1:1000), Bukhara Jews in Israel (prevalence 1:600) and Hispanics in New Mexico, Arizona Colorado and California [1-4]. OPMD is inherited, in most cases, as an autosomal dominant trait with complete penetrance. The disease is equally prevalent among both genders. The gene associated with the disease encodes the binding protein nuclear 1 protein (PABPN 1), a nuclear protein involved in pre-mRNA polyadenylation, transcription regulation, and mRNA nucleocytoplasmic transport. The mutation causing OPMD results in production of an abnormal poly (A) PABPN 1.

The disease is most often diagnosed in the fifth-sixth decades of life and progresses throughout the patient's life. By the age of 70, the majority of patients suffer from all or some of the following, symptoms: severe dysphagia, ptosis, tongue atrophy and weakness, lower and upper limb proximal weakness, dysphonia, limitation in upward gaze and facial muscle weakness. As ptosis becomes more pronounced patients adapt the "astronomer posture" tilting of the head and upward gaze—further aggravating the dysphagia. The dysphagia starts with difficulty in swallowing solid food and progresses to liquids as well. As the dysphagia becomes more severe, patients become malnourished, cachectic, dehydrated and suffer from repeated aspiration pneumonia. OPMD does not seem to shorten life expectancy but is associated with severe debilitation and reduced quality of life.

There is no medical treatment or potential cure for OPMD. Current therapeutic strategies are confined to surgical interventions aimed at alleviating ptosis. Repeated cricopharyngeal dilatations are frequently used to relieve dysphagia. Myotomy of the upper esophageal sphincter muscles has also been employed. These procedures may provide only temporary relief and do not affect the progression of the disease that eventually leads to severe difficulty in swallowing, recurrent aspiration with increasing risk of aspiration pneumonia and severe weight kiss which are the most common causes of mortality in OPMD patients.

Accordingly, there is an urgent need for compositions and therapeutic methods for alleviating the signs and symptoms of oculopharyngeal muscular dystrophy.

Although there are controversies regarding the specific role of protein aggregates in mechanisms underlying cell degeneration, a widely accepted view is that protein aggregates, the aggregation process and/or early oligomeric species are toxic and pivotal to degenerative pathology. An important piece of evidence was provided by studies showing the neurodegenerative process can be shut down and even reversed if caught in an early stage [5]. Furthermore, newer studies have shown that turnover of many culprit proteins is rapid rather than slow [6, 7] and that inclusion formation is reversible as well as ensuing neurotransmitter and, most importantly, behavioral abnormalities.

One of the new therapeutic strategies is to enhance the native cellular defense mechanisms against misfolded and aggregated proteins, for example using molecular chaperones which facilitate normal folding and refolding of abnormal conformations back to the native state [8]. Drugs such as geldanamycin can modulate and enhance chaperone levels [9]. Geldanamycin, however, has substantial toxicity and does not penetrate well the blood-brain barrier. It is also possible to stimulate proteasome activity, although this approach might have the danger of altering the turnover of molecules normally regulated by proteasome degradation. In addition, oral administration of the disaccharide trehalose, a disaccharide known for its protein stabilizing effect, has been shown in HD mouse model to reduce polyglutamine aggregates, improve motor dysfunction and extend survival [10]. More recently, these findings have been reproduced upon oral administration of trehalose in a mouse model of OPMD [11].

Trehalose, a glucose disaccharide (α-G-glucopyranosyl α-D-glucopyranoside), is found in many plants, fungi, bacteria, insects and other invertebrates, where it serves as a natural excipient. Due to its unique physical and biochemical properties demonstrated in its ability to sustain and preserve a wide array of biological molecules, trehalose has found its use in several food and cosmetic products and most notably in therapeutic products. Trehalose is an approved ingredient in all major markets designated as GRAS food ingredient by the FDA [12].

Currently a clinical study is being conducted in the US which examines the effect of large amounts of orally-administered trehalose in the prevention of arterial aging. In this study, the researchers compare the effect of Trehalose or Maltose or a combination of the two drugs on a bio marker associated with arterial aging [17].

GENERAL DESCRIPTION

In one of its aspects the presently disclosed subject matter provides a method for treating or alleviating a disease associated with abnormal protein aggregation and/or inclusion bodies formation in myocytes, neurons and other cells or extracellular compartments, or at least one symptom associated therewith, in a human subject in need thereof comprising parenterally administering to said subject a therapeutically effective amount of trehalose or a pharmaceutical formulation comprising a therapeutically effective amount of trehalose.

In the above and other embodiments the disease in accordance with the presently disclosed subject matter is any one of poly-alanine aggregation disorder, poly-glutamine aggregation disorder and a tauopathy, for example any one of oculopharengeal muscular dystrophy (OPMD), spinocerebellar ataxias (SCA), Friedreich's ataxia, spinal and bulbar muscular atrophy (SBMA), Huntington's disease, Parkinson's disease, Alzheimer's disease and amyotrophic lateral sclerosis (ALS), dentatorubral-pallidoluysian atrophy (DRPLA), Pick's disease, Corticobasal degeneration (CBD), Progressive supranuclear palsy (PSP) and Frontotemporal dementia and parkinsonism linked to chromosome 17 (FTDP-17).

In the above and other embodiments, the pharmaceutical formulation in accordance with the presently disclosed subject matter is an injectable solution for parenteral administration, in particular for intravenous, intramuscular and intraperitoneal administration.

In some embodiments, the pharmaceutical formulation in accordance with the presently disclosed subject matter comprises trehalose as sole active ingredient, and optionally further comprises at least one pharmaceutically acceptable additive, carrier, excipient or diluent.

In all embodiments the concentration of trehalose in the formulation in accordance with the presently disclosed subject matter is between about 0.1% (w/v) to about 50% (w/v), in particular about 10% (w/v).

In some embodiments the pharmaceutical formulation comprising trehalose in accordance with the presently disclosed subject matter has an osmolality of from about 280 to about 330 mOsm/Kg.

In the above and other embodiments the pharmaceutical formulation in accordance with the presently disclosed subject matter comprises less than 0.74 endotoxin units per ml solution.

The therapeutically effective amount of trehalose in accordance with the presently disclosed subject matter is from about 1 gram to about 100 gram for each single injection and no more than about 1 gram/kg body weight of said subject per day.

In other embodiments the therapeutically effective amount of trehalose or trehalose comprised in said pharmaceutical formulation is administered once daily at from about 10 mg/kg/day to about 1 gram/kg/day of trehalose.

In further embodiments the therapeutically effective amount of trehalose or trehalose comprised in said pharmaceutical formulation in accordance with the presently disclosed subject matter is administered at a single dose of 5, 8, 15, 30, 40 or 50 grams of trehalose.

The therapeutically effective amount of trehalose or pharmaceutical formulation comprising thereof according to the present disclosure may be administered chronically or periodically.

In the above and other embodiments the therapeutically effective amount of trehalose or pharmaceutical formulation comprising thereof according to the present disclosure is administered at a frequency of between once daily to once per month.

In further embodiments the therapeutically effective amount of trehalose or trehalose comprised in said pharmaceutical formulation according to the present disclosure is administered at a single injection administration once a week.

In still further embodiments the therapeutically effective amount of trehalose or pharmaceutical formulation comprising the same in accordance with the presently disclosed subject matter is intravenously administered at a single dose of from about 5 to about 35 grams of trehalose, which may be administered once daily, once every other day, twice a week, once a week, once every two weeks, once every three weeks or once a month.

In the above and other embodiments the pharmaceutical formulation in accordance with the presently disclosed subject matter is an injectable solution and wherein the rate of administration is such that the maximum endotoxin level is less than 5 endotoxin units per kilogram of body weight per hour.

In some embodiments administration of the therapeutically effective amount of trehalose comprised in said pharmaceutical formulation as herein defined, which is adapted for intravenous administration, is completed within from about 75 to about 120 minutes, specifically within less than 90 minutes.

In other embodiments administration in accordance with the presently disclosed subject matter comprises a dosing regimen of equal doses, or gradually increasing doses, or gradually decreasing closes of trehalose or pharmaceutical formulation comprising the same.

In another one of its aspects the presently disclosed subject matter provides trehalose or a pharmaceutical formulation comprising same, for use in a method for treating or alleviating a disease associated with abnormal protein aggregation and/or inclusion bodies formation in myocytes, neurons and other cells or extracellular compartments or at least one symptom associated therewith, in a human subject in need thereof, said method comprising parenterally administering to said subject a therapeutically effective amount of trehalose or a pharmaceutical formulation comprising the same.

In a further aspect the presently disclosed subject matter provides an aqueous pharmaceutical formulation comprising a therapeutically effective amount of trehalose as a sole active ingredient, wherein the formulation has a pH about 4.5 to 7.0 and contains less than 0.74 endotoxin units per ml and wherein said pharmaceutical formulation is adapted for parenteral administration.

The presently disclosed subject matter further provides a kit comprising:
(a) pharmaceutically acceptable trehalose or active derivative thereof;
(b) at least one pharmaceutically acceptable additive, carrier, excipient and diluent;
(c) means for preparing an injectable aqueous solution of the trehalose by mixing said trehalose with at least one of said additive, carrier, excipient and diluent;
(d) means for parenterally administering said injectable solution to a patient in need;
(e) instructions for use.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

A graph showing the fluctuations in the plasma concentration of trehalose administered intravenously (iv) or orally (po) to rats, during 8 hours post administration.

Figure 2:
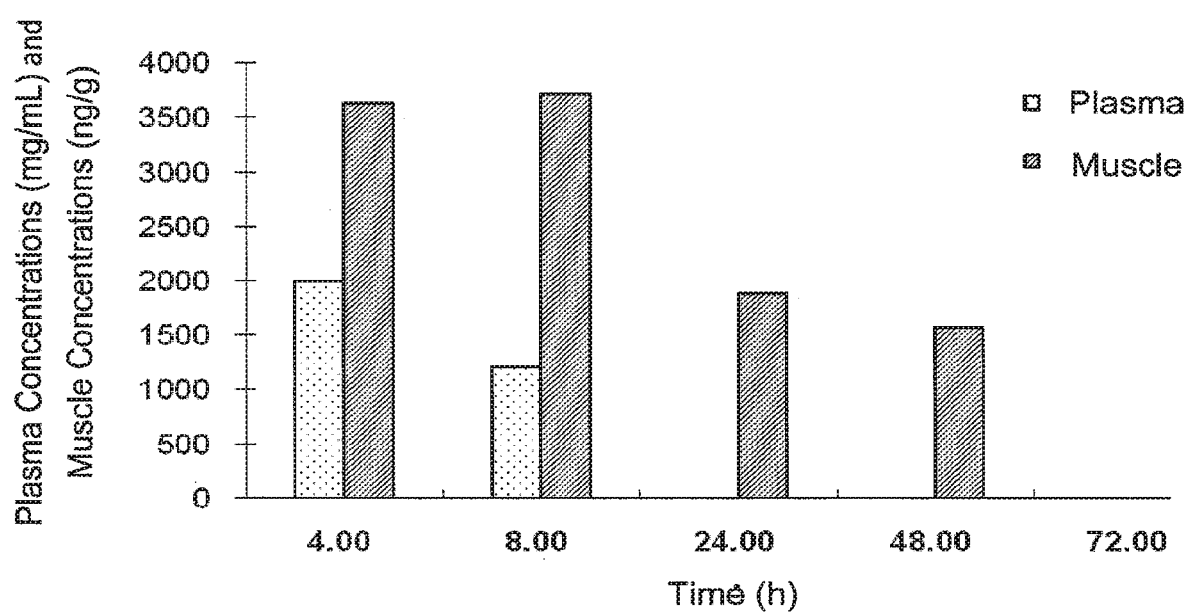

FIG. 2 Plasma and muscle concentrations trehalose after intravenous administration A bar graph showing the fluctuations in plasma and muscle concentrations of trehalose administered intravenously (1 g/kg) to rats, during 72 hours post administration.

DETAILED DESCRIPTION OF EMBODIMENTS

The presently disclosed subject matter is based on the surprising finding that upon parenteral, e.g. intravenous administration of an aqueous formulation comprising trehalose, therapeutically effective amounts of trehalose reached the plasma and accumulated in muscle of the tested animals as compared to plasma and muscle levels of trehalose obtained following oral administration of such formulations.

Trehalose is known for its ability to sustain and preserve a wide array of biological molecules. Trehalose has been used in a variety of research applications and is contained in several commercially available therapeutic products, including Herceptin, Avastin, Lucentis, and Advate, where it serves mainly as a lyoprotectant. Although trehalose is widely used as an excipient/additive together with another active ingredient, its use as a therapeutically active ingredient per se is rather exceptional.

Trehalose is capable of inhibiting intra-cellular aggregation of abnormal proteins associated with neurodegenerative diseases and myopathies. The leading example is the aggregation-suppressing effect of trehalose on the mutant huntingtin, a polyglutamine protein causing Huntington's disease (HD). Oral administration of trehalose to transgenic HD mice (0.2%-5% trehalose in drinking water consumed spontaneously in the course of 5-9 weeks) led to inhibition of formation of intra-nuclear huntingtin aggregates in the brain and liver and, more importantly led to improvement of HD-related motor symptoms.

Interestingly, therapeutic use of trehalose, especially in the context of neuronal and muscular diseases, is significantly precluded by the fact that trehalose is hydrolyzed by the intrinsic enzyme trehalose at the epithelial brush border in the small intestine [13, 14], due to which only a small fraction of any enterally administered dose reaches blood stream, neuronal or muscle-tissues. The present disclosure aims at introducing a novel therapeutic regime using parenteral administration of trehalose, thereby achieving higher bioavailability and therapeutic efficacy in the treatment of myopathic and neurodegenerative diseases associated with abnormal protein aggregation, specifically polyalanine polyglutamine and tauopathies, disorders, and OPMD in particular.

Thus the presently disclosed subject matter provides a method for treatingOr alleviating a disease associated with abnormal protein aggregation and/or inclusion bodies formation in myocytes, neurons and other cells or extracellular compartments, or at least one Symptom associated therewith, in a human subject in need thereof comprising parenterally administering to said subject, a therapeutically effective, amount of trehalose, or a pharmaceutical formulation comprising a therapeutically effective amount of trehalose.

As herein defined the term "disease associated with abnormal protein aggregation and/or inclusion bodies formation in myocytes, neurons and other cells or extracellular compartments" refers to any disease associated with protein aggregation or protein misfolding, where the common underlying biological feature of these diseases being the aggregation of certain peptides and proteins, thereby generating a cascade of pathological events, including the secondary aggregation of various other proteins and the consequent failure of protein homeostasis to preserve normal biological function.

The term "treating or alleviating" as herein defined refers to achieving a therapeutic effect, ameliorating, relieving or reducing the severity and/or frequency of at least one sign or symptom associated with diseases as herein defined, elimination of signs or symptoms and/or underlying cause, prevention of the occurrence of symptoms and/or their underlying cause (e.g., prophylactic therapy), improvement or remediation of damage and eliminating or reducing the extent of protein aggregation.

Symptoms associated with the diseases as herein defined include, but are not limited to, drooping eyelids (a condition known as "ptosis"), difficulty in swallowing (called "dysphagia"), muscle fatigue, movement/motion disorders and cognitive disorders to name but few.

In particular, where the disease to be treated is OPMD, the formulations and methods described herein are useful in the treatment of the signs and symptoms of OPMD. Signs and symptoms of OPMD include severe dysphagia ptosis, tongue atrophy and weakness, lower and upper limb proximal weakness, dysphonia, limitation in upward gaze and facial muscle weakness.

As known in the art, ample diseases and disorders are defined as "disease associated with abnormal protein aggregation and/or inclusion bodies formation in myocytes, neurons and other cells or extracellular compartments". For example, the presently disclosed subject matter provides a method for treating or alleviating a disease associated with abnormal protein aggregation which is a neurodegenerative disorder, a poly-glutamine or a poly-alanine aggregation disorder, a protein codon reiteration disorder, a myopathy, and a tauopathy, to name but few.

The term "neurodegenerative disorder" as herein defined refers to hereditary or sporadic conditions characterized by progressive nervous system dysfunction, specifically disorders of this group that are associated with formation of abnormal protein aggregates, also known as inclusion bodies formation. Examples for a neurodegenerative disorder which is associated with abnormal protein aggregation are Amyotrophic lateral sclerosis (ALS), Alzheimer's disease, Parkinson's disease and others.

The terms "poly-glutamine", "poly-alanine aggregation disorder" or "protein codon reiteration disorder" as herein defined refer to disorders associated with formation of intracellular polyglutamine or polyalanine aggregates, preferably referring to oculopharyngeal muscular dystrophy (OPMD), Huntington's disease (HD), spinal and bulbar muscular atrophy (SBMA), dentatorubral-pallidoluysian atrophy (DRPLA) and spinocerebellar ataxia (SCA).

The term "myopathy" as herein defined refers to inherited or acquired degenerative disease involving atrophy of the muscle fibers, in the context of present disclosure particularly referring to OPMD.

The term "tauopathy" as herein defined refers to neurodegenerative diseases associated with tau-pathology, prototypic intracellular aggregation of tau microfilaments, in the context of present disclosure particularly referring to Pick's disease, Corticobasal degeneration (CBD), progressive supranuclear palsy (PSP) and frontotemporal dementia and parkinsonism linked to chromosome 17 (FTDP-17).

Tauopathies are known as diseases caused by mutations leading to misfolding of Tau microtubule-associated protein that binds and stabilizes microtubules in neuronal cells. Tau pathology is a prominent feature of the sporadic Alzheimer's disease (AD), but is also seen in a variety of other related neurodegenerative diseases, such as Pick's disease, Corticobasal degeneration (CBD), Progressive supranuclear palsy (PSP) and Frontotemporal dementia and parkinsonism linked to chromosome 17 (FTDP-17). More than 30 different inherited mutations or nucleotide substitutions in the FTDP-17 gene on chromosome 17q21 have been related to neurodegenerative disease manifesting a prototypic intracellular aggregation of tau microfilaments. Tau mutation and by analogy tau dysfunction in inherited and, in sporadic diseases may be pathogenic through mechanisms involving both loss of function (decreased microtubules stabilization) and toxic gain of function (increased fibril formation).

Thus in the above and other embodiments the disease is any one of poly-alanine aggregation disorder, poly-glutamine aggregation disorder and a tauopathy.

In the above and other embodiments the disease is as herein defined is any one of oculopharengeal muscular dystrophy (OPMD), spinocerebellar ataxias (SCA), Friedreich's ataxia, spinal and bulbar muscular atrophy (SBMA), Huntington's disease, Parkinson's disease, Alzheimer's disease and amyotrophic lateral sclerosis (ALS), dentatorubral-pallidoluysian atrophy (DRPLA), Pick's disease, Corticobasal degeneration (CBD), Progressive supranuclear palsy (PSP) and Frontotemporal dementia and parkinsonism linked to chromosome 17 (FTDP-17).

In some embodiments the disease is as herein defined is oculopharengeal muscular dystrophy (OPMD).

As indicated above, OPMD is caused by inherited abnormal expansions of polyalanine in the poly A binding protein nuclear 1 protein (PABPN1) leading to PABPN1 misfolding and formation of tubule-filamentous, inclusions/aggregates in nuclei of the affected muscle cells. Oral administration of trehalose to transgenic OPMD mice (2% trehalose in drinking water consumed spontaneously during 4-6 months) was shown to significantly reduce aggregation formation and toxicity of the mutant PABPN1 in myocytes. Overall, oral trehalose was shown to delay the OPMD onset, attenuate the disease phenotype, decrease polyalanine protein aggregate formation and decrease cell death, thus suggesting that trehalose may be a potent anti-aggregation therapy for OPMD and other protein codon reiteration disorders.

As indicated in the accompanying Examples, the inventors have shown that trehalose can be successfully delivered to muscle, which is the target organ in treatment of various diseases and disorders as herein defined, for example but not limited to OPMD.

Huntington's disease and OPMD share a common genetic basis as both are caused by inherited, trinucleotide expansion, mutations in a disease causative gene. The HD gene (HTT), located on chromosome 4p16, contains repetitive trinucleotide sequences (CAG)n encoding for a polyglutamine (poly Q) stretch. While the normal HTT gene variants contain 7-35 repeats, HD-related variants are above that range and the extent of repeat expansions is correlated to the severity and earlier onset of HD symptoms (the effect termed anticipation). Analogous (CAG)n repeat expansions mutations were associated with other polyglutamine disorders, such as SBMA, DRPLA and several ataxias belonging to the group of SCA. Similarly, the OPMD-related gene, PABPN1 on chromosome 14q11 contains trinucleotide repeats (CGC)n encoding polyalanine (poly A), wherein (CGC)6 repeats is the normal threshold above which OPMD is anticipated with an increased number of repeats.

Thus in other embodiments the disease is as herein defined is Huntington's disease.

In view of the apparent lack of medical therapy for HD, OPMD and other related disorders apart from medications that lessen some motor and psychiatric symptoms, therapies that directly interfere with the disease-causing mechanisms are sorely needed.

In some embodiments the disease is as herein defined is spinocerebellar ataxia (SCA). As known in the art there are many types of spinocerebellar ataxia, with the most common Spinocerebellar ataxia including Friedreich's ataxia, SCA 1,3,8, and more. Many SCAs fall under the category of polyglutamine diseases, which are caused when a disease-associated protein (i.e., ataxin-1, ataxin-3, etc.) contains a glutamine repeat beyond a certain threshold.

In other embodiments disease is as herein defined is spinal and bulbar muscular atrophy (SBMA). The disease SBMA, also known as spinobulbar muscular atrophy, bulbo-spinal atrophy, X-linked bulbospinal neuropathy (XBSN), X-linked spinal muscular atrophy type 1 (SMAX1), and Kennedy's disease (KD), as known in the art, is a debilitating neurodegenerative disease resulting in muscle cramps and progressive weakness due to degeneration of motor neurons in the brain stem and spinal cord.

In further embodiments disease is as herein defined is Huntington's disease, Parkinson's disease, Alzheimer's disease or amyotrophic lateral sclerosis (ALS).

Huntington's disease (HD) is a neurodegenerative genetic disorder that affects muscle coordination and leads to cognitive decline and psychiatric problems; Parkinson's disease is a degenerative disorder of the central nervous system; Alzheimer's disease (AD) is manifested by short term memory loss, confusion, irritability, aggression, mood swings, trouble with language, and long-term memory loss; and amyotrophic lateral sclerosis (ALS, also referred to as motor neuronal disease or Lou Gehrig's disease) is a neurodegenerative disease characterized by rapidly progressive weakness due to muscle atrophy and muscle spasticity, difficulty in speaking (dysarthria), swallowing (dysphagia), and breathing (dyspnea).

As indicated above, the presently disclosed subject matter provides a method for treating or alleviating a disease as herein defined in a human subject in need thereof comprising parenterally administering to said subject a therapeutically effective amount of trehalose or a pharmaceutical formulation comprising same.

In the above reports of trehalose as a therapeutic agent for diseases associated with protein aggregation, there is need for exceedingly high and continuous oral intake of trehalose in order to achieve the desired therapeutic effect in neuronal or muscle tissue, due to its in the intestines.

The instant disclosure is directed to a therapeutic regimen using trehalose that is administered to a subject in need by parenteral administration.

Thus in some embodiments the pharmaceutical formulation as herein defined is an injectable solution for parenteral administration.

The term "subject in need thereof" refers to a subject suffering from a disease as herein defined, for example but not limited to HD or OPMD or another polyglutamine or polyalanine aggregation disorder.

The therapeutically effective amount of trehalose can be from about 10 mg to about 1,000 mg/Kg body weight per day. The trehalose can be comprised as active ingredient in a pharmaceutical formulation suitable for parenteral administration. Administration can be based on a daily regime as a single dose or multiple doses by a single parenteral administration or as multiple doses by multiple parenteral administrations, respectively. Alternatively or additionally, administration can be periodic, for example every other day, three times weekly, twice weekly, once weekly, or once monthly, and frequency of administration can be varied according to the patient condition.

The term parenterally as, herein defined refers to a route of administration where the desired effect is systemic and the active agent (herein defined as trehalose), is administered by routes other than the digestive tract, for example intravenous, intramuscular and intraperitoneal administration.

As indicated above, trehalose is known in the art as a lyoprotectant. As such the safety and toxicity of trehalose has been extensively investigated, and the substance was found to be safe when administered both orally and intravenously, in doses that are substantially higher than the intended therapeutic dose.

As shown in the Examples below, a pharmaceutical formulation comprising trehalose as sole active ingredient was parenterally administered resulting in relatively high plasma and muscle levels.

Thus, in some embodiments the pharmaceutical formulation as herein defined comprises trehalose as sole active ingredient, and optionally further comprises at least one pharmaceutically acceptable additive, carrier, excipient or diluent.

In other words, in the presently disclosed subject matter trehalose is the only active agent or ingredient. Notwithstanding the above, trehalose or a pharmaceutically formulation comprising same may be used in combination with other therapies or treatments for treating or alleviating a disease associated with abnormal protein aggregation.

The term "trehalose" as herein defined refers to a disaccharide glucose α-G-glucopyranosyl α-D-glucopyranoside. The term trehalose also refers to any active derivative of trehalose, for example hydrides and salts thereof.

Trehalose is a naturally occurring disaccharide comprised of a 1,1 linkage of two D-glucose molecules. It is a non-reducing sugar that is not easily hydrolyzed by acid. Its molecular formula is $C_{12}H_{22}O_{11}$ and its molecular weight is 342.31 Dalton. Other-names used to describe the α, α form, the isomer commonly referred to as 'trehalose', are α,α-Trehalose, α-δ-glucopyranosyl, α-δ-glucopyranoside, mushroom sugar, mycose.

As indicated above, trehalose is well known for its protein-stabilizing properties. It is used extensively in many applications as a stabilizer of frozen food, in freeze-drying of biological systems and cells, as a stabilizer of therapeutic parenteral proteins and as an excipient in tablets and IV solutions. Trehalose is recognized as a GRAS (Generally Regarded as Safe) food ingredient by the FDA and is listed on the USP-NF (United States Pharmacopoeia National Formulary), EP (European Pharmacopoeia) and JP (Japanese Pharmacopoeia).

Like all disaccharides, trehalose is metabolized at the epithelial brush border to two D-glucose molecules. Less than 0.5% of ingested trehalose is absorbed into the blood stream where it is further metabolized by liver and kidney by trehalose. Oral trehalose in amounts exceeding 40-50 gram per day causes diarrhea and bloating. Thus in order to achieve therapeutic amounts of trehalose in the muscle cells it was necessary to circumvent the massive metabolism in the gastrointestinal tract (GI) tract. Therefore the inventors developed an intravenous (IV) solution of trehalose.

The term "formulation" as herein defined refers to a composition comprising trehalose as active ingredient and optionally further comprising additional active ingredient such as anti-inflammatory agent, and at least one pharmaceutically acceptable additive, carrier, excipient or diluents as well known in the art. This formulation may further comprise a trehalose (a glycoside hydrolase enzyme catalyzing the conversion of trehalose to glucose found in the intestine, kidney and liver) inhibitor, i.e. competitive or other inhibitor of the trehalose enzyme.

Particular pharmaceutical formulations are suitable for parenteral administration, specifically injectable solutions; wherein the concentration of trehalose in said formulation is between about 0.1% (weight/volume) to about 50% (weight/volume), more specifically wherein the concentration of trehalose in the formulation as herein defined is, but is not limited to, about 8%, 9%, 10%, 11%, 12%, 13%, 14%, 15%, 20% or 25% (weight/volume).

When referring to trehalose, the term trehalose encompasses not only the specified molecular entity but also its pharmaceutically acceptable, pharmacologically active analogs, including, but not limited to, salts, polymorphs, esters, amides, prodrugs, adducts, conjugates, active metabolites, and the like.

Thus the active agent, trehalose, may be administered in the form of the compound per se as well as in the form of a salt, polymorph, ester, amide, prodrug, derivative, or the like, provided the salt, polymorph, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present formulations either as the racemate or in enantiomerically pure form.

Salts are compounds that ionize in aqueous solutions and may be employed, for example, to adjust the tonicity of the solution. If the active agent is present in the forth of a salt, additional salts may be added to the composition in order, for example, to effect ion exchange with the active agent. Salts suitable for use with the compositions described herein are known in the art and include, for example, lithium, sodium, potassium, calcium, and magnesium salts having appropriate counterions that may be selected from chloride, bromide, iodide, carbonate, phosphate, nitrate, silicate, sulfate, phosphite, nitrite, sulfite, and the like.

Buffers are compounds or solutions that are employed to aid in maintaining the concentration of an analyte within a desired range. For example, pharmaceutically acceptable pH buffers are used to maintain the acidity or basicity of a solution within a pharmaceutically acceptable range. Buffers for use in the compositions disclosed herein may be any known or hereafter discovered buffer.

Excipients are inactive ingredients that may be employed in the compositions described herein for a variety of reasons. A wide range of excipients are described in the literature (e.g., Rowe et al., Handbook of Pharmaceutical Excipients, McGraw Hill, 2006).

Additives and diluents are well known in the art.

In some specific embodiments the pH of the formulation is about 4.5 to 7.0; the osmolality of the formulation is about 280-330 mOsm/kg, the formulation contains less than 1.0, 0.9, 0.8, 0.7, 0.6, 0.5, 0.4, 0.3, 0.2, 0.1 or less endotoxin units per mL and the aqueous formulation is about 50%, 40%, 30%, 20%, 10%, 5% or less trehalose (w/v).

Thus the presently disclosed trehalose delivery systems, for example formulations comprising trehalose as sole active ingredient, can generally comprise, a buffering agent (pH adjusting additives), an agent which adjusts the osmolality thereof, and optionally, one or more pharmaceutically acceptable carriers, excipients and/or additives as known in the art. Supplementary pharmaceutically acceptable active ingredients can also be incorporated into the formulations.

For formulations as herein defined administered as aqueous or other solvent-based dosage forms (e.g., for parenteral administration), a variety of liquid carriers may be used, in particular water or saline. Aqueous solutions may include salts, buffers, and the like. The carrier can be solvent or dispersion medium suitable for parenterally-administrable compositions containing, for example, water, saline, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. Water is an essential additive (or carrier).

Thus as used herein the term "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated. It is contemplated that the active agent can be delivered by any acceptable parenteral route and in any pharmaceutically acceptable dosage form.

For purposes of parenteral administration, formulations in suitable oil such as sesame or peanut oil or in aqueous propylene glycol can be employed, as well as sterile aqueous solutions of the corresponding water-soluble salts. Such aqueous formulations may be suitably buffered, if necessary, and the liquid diluent first rendered isotonic with sufficient saline or glucose. These aqueous formulations are especially suitable for intravenous, intramuscular, subcutaneous and intraperitoneal injection purposes. In this connection, the sterile aqueous media employed are all readily obtainable by standard techniques well-known to those skilled in the art.

Methods of preparing various pharmaceutical formulations with a certain amount of active ingredient are known, or will be apparent in light of this disclosure, to those skilled in this art.

As described in the accompanying Examples, the inventors have prepared a specific injectable, aqueous formulation comprising trehalose, that is currently used in an on-going study in OPMD patients, as described below in Example 6 (and may be used for treatment of other diseases, associated with abnormal protein aggregation).

Given the fact that over 99.5% of the trehalose is not absorbed into the blood stream, and that oral amounts of trehalose higher than 50 g a day in humans frequently cause diarrhea, bloating and discomfort as indicated above, the most effective way to ensure that adequate amounts of trehalose indeed reach the muscle cells is to circumvent the extensive gut metabolism and administer trehalose by intravenous (IV) solution.

The disclosed injectable solution of trehalose can be intravenously administered to OPMD patients at a single administration (injection) during about 75 to 120 minutes, for example 90 minutes, every day, every other day, twice a week, once a week, once in 10 days, once every two weeks or once a month, for a defined number of administrations as will be determined by the attending physician.

Based on well-known pharmacokinetic profile of trehalose, initial once a Week, 24-week IV therapy will enable trehalose to enter the muscle cells and potentially exert its therapeutic effect, previously demonstrated in animal models. The amounts to be administered in the weekly injection are based on known safety studies as well as the rate of metabolism and clearance from the blood so as to enable trehalose to reach muscle cells before it is cleared from the blood.

The doses are calculated based on the expected plasma and tissue distribution of trehalose, effective concentration of trehalose in diseased cells and known safety closes in multiple animal studies.

Following initial treatment, once weekly administration can be chronic, at set time points, for spells of several or scores of weeks, for example additional consecutive 48 weeks, thus a total of 72 weeks of treatment, or administration can be periodic.

In some embodiments, the osmolality of the disclosed aqueous trehalose injectable pharmaceutical formulation is from about 280 to about 330 mOsm/Kg.

As indicated above, the inventors have shown successful delivery of trehalose to plasma and muscle by parenteral, specifically IV administration. Thus in some embodiments administration of trehalose or a pharmaceutical formulation comprising same may be in any one of intravenous, intramuscular and intraperitoneal administration.

In one embodiment the purified trehalose is substantially free of contaminants resulting from its enzymatic preparation process, such as organic solvents used in the process (e.g., ammonium, acetonitrile, acetamide or alcohols), TFA, ether or other contaminants. In this context "substantially" free of contaminants means that the contaminant content of any residual peptide originating from the enzymatic preparation process at the end of the purification process is preferably less than 0.5%, less than 0.3%, less than 0.25%, less than 0.1%, less than 0.05%, less than 0.04%, less than 0.03%, less than 0.02%, less than 0.01%, less than 0.005%, less than 0.003%, or less than 0.001% of the total weight of the trehalose. The content of contaminants can be determined by conventional methods such as gas chromatography.

In specific embodiments, the residual solvents in the purified trehalose are less than the limits set in the ICH guidelines, e.g., IMPURITIES: GUIDELINE FOR RESIDUAL SOLVENTS Q3C(R5) (available at: http://www.tga.gov.au/pdf/euguide/ich822602006.pdf) [15]). For example, the purified trehalose contains <5000 ppm ethanol (e.g., <140 ppm), and/or <3000 ppm methanol.

Endotoxins (also known as lipopolysaccharides (LPS) and lipoglycans) are large molecules consisting of a lipid and a polysaccharide composed of O-antigen, outer core and inner core joined by a covalent bond; they are found in the outer membrane of Gram-negative bacteria, and elicit strong immune responses in animals. Endotoxins are well-known contaminants in substances purified by using bacterial systems and their removal is thus crucial for safety of using therapeutic formulations comprising such substances.

As shown in the accompanying Examples, the presently disclosed formulation comprises less than 5 endotoxin units per kilogram of body weight of a patient administered with, the formulation, per hour of administration.

Thus in some embodiments the pharmaceutical formulation as hernia defined comprises less than 0.74 endotoxin units per ml solution.

Therapeutically effective amount as herein defined will depend on a number of factors and will vary from subject to subject and may be determined by considerations well known to a skilled person in the field of the invention (e.g. a skilled physician). Such factors include the severity of the symptoms, the patient's age, weight and general condition, and the judgment of the prescribing physician.

Generally, by the term "therapeutically effective amount" it is meant a nontoxic but sufficient amount of trehalose to provide the desired effect, namely the treating or alleviating a disease associated with abnormal protein aggregation and/or inclusion bodies formation in myocytes, neurons and other cells or extracellular compartments.

The term "therapeutically effective amount or pharmaceutical composition comprising thereof" is to be understood as the amount of trehalose comprised in the administered formulation. The amount of the formulation itself may vary according to the concentration of the trehalose comprised therein (namely, such that the concentration of trehalose in said formulation is between about 0.1% (w/v) to about 50% (w/v) and such that the maximum endotoxin level in administered formulation is less than 5 endotoxin units per kilogram of body weight per hour).

Therapeutically effective amount of trehalose refers to an amount of from about 1 grain to about 100 gram for each daily injection and no more than 1 g/kg body weight of said subject per day of a treated human subject. Amount may considerably vary. Thus the range can be from each of 10, 20, 50, 75, 100, 150, 200, 300 mg/Kg body weight per day up to each of 400, 450, 500, 550, 600, 650, 700, 750, 800, 850, 900, 950 and 1000 mg/Kg body weight per day.

Thus in other embodiments, therapeutically effective amount of trehalose as herein defined is from about 1 gram to about 100 gram for each single injection and no more than about 1 gram/kg body weight of said subject per day.

The terms "injection" and "infusion" are used interchangeably and refer to parenteral administration of the formulation as herein defined.

The therapeutically effective amount of trehalose or pharmaceutical composition comprising thereof is administered parenterally, and can be administered as a single dose or multiple doses, which may be identical or different, by a single administration per day, or multiple doses can be parenterally administered by multiple daily or weekly or monthly or more prolonged administrations.

A therapeutically effective amount of trehalose or pharmaceutical composition according to the above, administered IV, IP or IM, as a single dose or multiple doses, which may be identical or different, by a single administration per day, or optionally as multiple doses, which may be identical or different, by multiple administrations per day, or further optionally in a dosing regimen of equal doses, or gradually increasing doses, or gradually decreasing doses, or further chronically or periodically.

Optimal dosing schedules, may be calculated from measurements of drug accumulation in the body of the patient. Optimal doss can be determined by dosing methodologies and repetition rates. In general, dosage is calculated according to body weight, and may be given once or more daily, weekly, monthly or yearly, or even once every few years. Persons of ordinary skill in the art can readily estimate repetition rates for dosing based on measured residence times and concentrations of the combined composition of the invention in bodily fluids or tissues. Following successful treatment, it may be desirable to have the patient undergo maintenance therapy to prevent the recurrence of the disease state, wherein the combined composition of the invention is administered in maintenance doses, once or more daily.

In some embodiments the therapeutically effective amount of trehalose or pharmaceutical formulation comprising same as herein defined is administered chronically.

The term "chronically" as herein defined refers to a constant regime of administration occurring at a predetermined frequency. Thus administration may be based for example on a daily, weekly or monthly regime as a single parenteral dose or multiple parenteral, specifically intravenous doses.

In some embodiments the frequency as herein defined is of between once daily to once per month, namely said therapeutically effective amount of trehalose or pharmaceutical formulation comprising thereof is administered at a frequency of between once daily to once per month.

In other embodiments the frequency as herein defined is every day (daily), namely seven times per week or six, five, four or three times per week, twice or once per week, once in every two weeks, once in every three weeks or once per month.

In specific embodiment the frequency as herein defined is once per week. In other embodiments the therapeutically effective amount of trehalose or trehalose comprised in said pharmaceutical formulation is administered at a single injection administration once a week.

In the above and other embodiments the therapeutically effective, amount of trehalose or trehalose comprised in said pharmaceutical formulation is administered once daily at from about 10 mg/kg/day to about 1 gram/kg/day of trehalose.

As indicated in the accompanying Examples, in an ongoing clinical study an aqueous injectable pharmaceutical formulation comprising trehalose is administered intravenously at a weekly dosing of 8, 15 or 30 gram per subject.

Thus in the above and other embodiments the therapeutically effective amount of trehalose or pharmaceutical formulation comprising the same is intravenously administered at a single dose of from about 5 to about 35 grams of trehalose, which may be administered once daily, once every other day, twice a week, once a week, once every two weeks, once every three weeks or once a month.

In further embodiments the therapeutically effective amount of trehalose or trehalose comprised in said pharmaceutical formulation is administered at a single-dose of 5, 8, 15, 30, 40 or 50 grams of trehalose.

In other embodiments the therapeutically effective amount of trehalose or a pharmaceutical formulation comprising the same is adapted for an injectable solution and wherein the rate of administration is such that the maximum endotoxin level is less than 5 endotoxin units per kilogram of body weight per hour.

By the term "rate of administration" it is meant the rate of infusion (or dosing rate).

In further embodiments the therapeutically effective amount of trehalose or a pharmaceutical formulation comprising the same is adapted for intravenous administration and said administration is completed within less than about 75 to 120 minutes, for example but not limited to within 90 minutes. The period of administration will also depend on the volume/amount of the disclosed injectable trehalose formulation to be administered.

Thus in some embodiments administration of the therapeutically effective amount of trehalose comprised in said pharmaceutical formulation adapted for intravenous administration is completed within from about 75 to about 120 minutes, specifically within less than 90 minutes.

In still further embodiments the administration of trehalose or a pharmaceutical formulation comprising the same comprises a dosing regimen of equal doses, or gradually increasing doses, or gradually decreasing doses of trehalose or pharmaceutical formulation comprising the same.

In some embodiments the therapeutically effective amount of trehalose or pharmaceutical formulation comprising thereof is administered periodically.

By the term "periodically" it is meant that the administration of trehalose may be conducted at consecutive chronic administration regimens as herein defined which may be separated in time by periods of "no treatment" (or "drug holiday", i.e. when the patient as herein defined stops taking the active agent for a certain period of time) according to the patient condition.

Determining the efficaciousness of the treatment as herein defined may be performed by any method known to a person skilled in the art. For example, when the disease to be treated is OPMD, efficaciousness of the treatment may be performed in association with any known method for diagnosing or treating OPMD. Alleviation of one or more signs or symptoms of OPMD indicates that the compound confers a clinical benefit.

Thus in some embodiments the disease according to the presently disclosed subject matter is OPMD and in such case efficaciousness of treatment as herein defined may be performed by monitoring patient's weight; performing a "drinking test", in which the patient is requested to drink 80 ml of ice-cold water, and the time which this volume has been fully consumed (in seconds) will be recorded; and by fiberoptic endoscopic evaluation of swallowing (FEES), which is a useful supplementary tool for studying dysphagia. The FEES procedure involves introducing a flexible fiberoptic endoscope transnasally to the patient's hypopharynx where the clinician can clearly view laryngeal and pharyngeal structures. The patient is then led through various tasks (e.g. food and liquid boluses) to evaluate the sensory and motor status of the pharyngeal and laryngeal mechanism. Information obtained from this examination includes ability to protect the airway, ability to sustain airway protection for a period of several seconds, ability to initiate a prompt swallow without spillage of material into the hypopharynx, timing and direction of movement of the bolus through the hypopharynx, ability to cleat the bolus during the swallow, presence of pooling and residue of material in the hypopharynx, timing of bolus flow and airway protection, sensitivity of the pharyngeal/laryngeal structures and the effect of anatomy on the swallow.

Additional tests for evaluating efficaciousness of treatment of OPMD include the SWAL-QOL test (a 44 item tool that asks patients to rate Several factors about 10 quality-of-life concepts related to swallowing on a 5 point scale) that was developed for measuring objectively a patient's perspective of swallowing and the muscle strength assessment (assessment of weakness of the proximal muscles, including "stair climb" test, "30 second sit-to-stand" test, "30 second weight arm raise" test, etc.).

The term "subject in need thereof" as herein defined is a subject suffering from a disease or disorder as herein defined, namely a disease associated with abnormal protein aggregation and/or inclusion bodies formation in myocytes, neurons and other cells or extracellular compartments.

In certain embodiments, the present disclosure provides a formulation comprising trehalose or a physiologically acceptable derivative thereof wherein trehalose (or derivative thereof) or at least a portion of the trehalose or derivative thereof is formulated for sustained and/or controlled release and a portion of the trehalose or derivative thereof is formulated for immediate release, when administered to a subject.

In certain embodiments, effective serum levels of The active ingredient trehalose or derivative thereof are achieved within from about 10 to about 20 or 30 or 40 or 50 or 60 minutes following trehalose administration. In certain embodiments, effective serum levels of the active ingredient are achieved within from about 5 to about 20 or 30 or 40 or 50 or 60 minutes following trehalose administration. In certain embodiments, effective serum levels of the active ingredient are achieved within from about 20 to about 20 or 30, or 40 or 50 or 60 minutes following trehalose administration. In certain embodiments, effective serum levels of the active ingredient are achieved within about 5, 10, 15, 20, 30, 40, 50 or 60 minutes following trehalose-administration.

The present inventors have developed innovative approaches for the administration of trehalose based on parenteral routes. These approaches provide for a rational design of delivery systems (e.g. formulations) with desired properties based on the meticulous selection of the carrier, e.g. appropriate surfactants/co-surfactants composition or micro/nano particles (such as liposomes or nano-liposomes) or polymer entrapping the active ingredients, or other additives or excipients, for the delivery system of interest.

The parenteral ways include subcutaneous and transdermal (diffusion through the intact skin) administration. In certain embodiments, the formulations of the invention, are administered by invasive modes of treatment such as by intravenous, intramuscular and like administration.

Another way of administration can make use of red blood cells loaded with high quantities of trehalose, which are known in the art. It is currently known that loading red blood cells with high amounts of trehalose enhances their viability. Such red blood cells, highly loaded with trehalose can serve as a vehicle for intravenous delivery of trehalose to a subject in need, in accordance with the present disclosure.

Administration of trehalose for medical uses requires safe and efficient delivery systems. The present disclosure provides delivery systems (e.g. formulations for parenteral administration) for safe delivery of a variety of substances due to their special physico-chemical features. The delivery systems significantly enhance efficiency and quality of trehalose absorption based on its unique physicochemical features, which enables lower concentrations or amounts of active substance to be delivered to a subject in a biologically active form. The present delivery systems provide for the direct access of the active substance to the tissues and thus provide immediate or near-immediate effects of trehalose to the subject in need thereof.

Accordingly, in certain embodiments, the present invention provides a pharmaceutical delivery system for the improved administration of trehalose or physiologically active derivative thereof, comprising as the active ingredient said trehalose or physiologically active derivative thereof in a suitable carrier for fast restoration of relief of symptoms of the disease of the treated subject.

In certain embodiments, the drug delivery systems may provide the active substance in a controlled release mode. In certain embodiments, the drug delivery systems of the invention may further comprises at least one additional pharmaceutically active agent.

The presently disclosed delivery systems can generally comprise a buffering agent, an agent which adjusts, the osmolality thereof, and optionally, one or more pharmaceutically acceptable carriers, excipients and/or additives as known in the art. Supplementary pharmaceutically acceptable active ingredients can also be incorporated into the compositions. The carrier can be solvent or dispersion medium suitable for parenterally-administrable compositions containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As indicated above, the present trehalose delivery system can be administered in controlled-, sustained- or delayed-release formulations. Any controlled or sustained release method known to those of ordinary skill in the art may be used with the formulations and methods of the presently disclosed subject matter such as those described in Langer 1990 [16]. Such method comprises administering a sustained-release composition or a coated implantable medical device so that a therapeutically effective dose of the composition of the invention is continuously delivered to a subject of such a method. Sustained release may also be achieved using a patch designed and formulated for the purpose. Controlled or sustained-release compositions include formulation in lipophilic depots (e.g., fatty acids, waxes, oils). Also comprehended by the invention are particulate compositions coated with polymers (e.g., poloxamers or poloxamines). Sustained release formulae or devices, or any topical formulations, may additionally contain compositions to stabilize the composition or permeate physiological barrier such as skin or mucous membrane. Exemplary additional components may include any physiologically acceptable detergent, or solvent such as, for example, dimethylsulfoxide (DMSO).

In certain embodiments, the trehalose in the present compositions can be formulated for sustained or controlled release over a period of at least 0.5, 1, 2, 3, 4, 5, 6, 7, 8, 9, 10, 11 or 12 hours. In certain embodiments, the trehalose in the present compositions can be formulated for sustained or controlled release over a period of about 0.5, 1, 2, 3, 4, 5, 7, 8, 9, 10, 11 or 12 hours. In certain embodiments, the trehalose in the present compositions can be formulated for sustained or controlled release over a period of between about 0.5 or 1 or 2 or 3 or 4 hours and about 5, 6, 7, 8, 9, 10, 11 or 12 hours. In certain embodiments, the trehalose in the present compositions can be formulated for sustained or controlled release over a period of between about 5 or 6 or 7 or 8 hours and about 9, 10, 11 or 12 hours.

In certain embodiments the trehalose in the present compositions can be in immediate, fast of burst release form.

In certain embodiments, the trehalose in the present compositions can be formulated to release up to 5, 10, 15, 20, 25, 30, 35, 40, 45, 50, 55, 60, 65, 70, 75, 80, 85, 90, 95, 99, 99.5 or 100% of the total trehalose in about 0.5, 1, 2, 3, 4, 5, 6, 7 or 8 hours. In certain embodiments, the trehalose in the present compositions can be formulated to release not less than 5, 10, 15, 20, 25, 30, 35, 40, 45, 50, 55, 60, 65, 70, 75, 80, 85, 90, 95, 99, 99.5 or 100% of the total trehalose in about 0.5, 1, 2, 3, 4, 5, 6, 7 or 8 hours.

In certain embodiments, the trehalose in the present compositions can be in a combination of sustained or slow release and immediate or fast or burst release forms. In certain embodiments, the relative proportion of sustained or slow release trehalose to immediate or fast release trehalose is, e.g., 1 to 99, 5 to 95, 10 to 90, 15 to 85; 20 to 80, 25 to 75, 30 to 70, 35 to 65, 40 to 60, 45 to 55, 50 to 50, 55 to 45; 60 to 40, 65 to 35, 70 to 30, 75 to 25, 80 to 20, 85 to 15, 90 to 10, 95 to 5, or 99 to 1.

In certain embodiments, a polymeric material is used to sustain or control release of trehalose. In certain embodiments, the type of polymeric material and the amount of which is used, have a strong influence on the rate of release of trehalose from the present compositions and delivery systems. Examples of polymers include both hydrophobic and hydrophilic polymers. Examples of hydrophobic polymers include, but are not limited to, ethyl cellulose and other cellulose derivatives, fats such as glycerol palmito-stearate, beeswax, glycowax, castorwax, carnaubawax, glycerol monostearate or stearyl alcohol, hydrophobic polyacrylamide derivatives and hydrophobic methacrylic acid derivatives, as well as mixtures of these polymers. Hydrophilic polymers include, but are not limited to, hydrophilic cellulose derivatives such as methyl cellulose, hydroxypropylmethyl cellulose, hydroxyethylcellulose, hydroxypropyl cellulose, carboxymethyl cellulose, sodium carboxymethylcellulose and hydroxyethyl methylcellulose polyvinyl alcohol, polyethylene, polypropylene, polystyrene, polyacrylamide, ethylene vinyl acetate copolymer, polyacrylate, polyurethane, polyvinylpyrrolidone, polymethylmethacrylate, polyvinyl acetate, polyhydroxyethyl methacrylate, as well as mixtures of these polymers. Furthermore, any mixture of one or more hydrophobic polymer and one or more hydrophilic polymer could optionally be used.

The trehalose contained in the present compositions and delivery systems can be entrapped in liposomes, micro- and nano-particles.

In certain embodiments, a polymeric material to be used in the present compositions and delivery systems is microcrystalline cellulose such as "Avicel PH 101" manufactured by FMC BioPolymer's. Alternatively, a polymeric material to be used in the present compositions and delivery systems is hydroxypropyl methylcellulose such as "Metholose" produced by Shin-Etsu Chemical Co. In certain embodiments, a polymeric material to be used in the present compositions and delivery systems is ethyl cellulose such as "Ethocel™" manufactured by The Dow Chemical Company. In certain embodiments, a polymeric material to be used in the present compositions and delivery systems is an acrylic polymer such as "Eudragit RS™" produced by Rohm GmbH. In certain embodiments, a polymeric material to be used in the present compositions and delivery systems is a colloidal silicone dioxide such as "Acrosil™" manufactured by Degussa. In certain embodiments, a polymeric material to be used in the present compositions and delivery systems is a Poly (Vinyl Acetate) such as "Kollicoat SR" manufactured by BASF. In certain embodiments, a polymeric material to be used in the present compositions and delivery systems is an ethyl acetate and vinyl acetate solution such as "Duro-Tak" manufactured by Delasco Dermatologic Lab & Supply, Inc.

In certain embodiments, delivery systems of the invention comprise delivery devices. In certain embodiments, the compositions of the invention are delivered by ail osmotic process at a controlled rate such as by an osmotic pump. The system may be constructed by coating an osmotically active agent with a rate controlling semipermeable membrane. This membrane may contain an orifice of critical size through which agent is delivered. The dosage form after coming into contact with aqueous fluids, imbibes water at a rate determined by the fluid permeability of the membrane and osmotic pressure of the core formulation. This osmotic imbibitions of water result in formation of a saturated solution of active material with in the core, which is dispensed at controlled rate from the delivery orifice in the membrane.

In certain embodiments, the compositions of the invention are delivered using biodegradable microparticles. In certain embodiment, the system to prepare microparticles consists of an organic phase comprised of a volatile solvent with dissolved polymer and the material to be encapsulated, emulsified in an aqueous phase. In certain embodiments, the biodegradable polymers that can be used for the microparticle matrix, comprises polylactic acid (PLA) or the copolymer of lactic and glycolic acid (PLAGA). The PLAGA polymer degrades hydrolytically over time to its monomeric components, which are easily removed from the body through natural life processes.

The preparation may also contain an absorption enhancer and other optional components. Examples of absorption enhancers include, but are not limited to, are cyclodextrins, phospholipids, chitosan, DMSO, Tween, Brij, glycocholate, saponin, fusidate and energy based enhancing absorption equipment.

Optional components present in the dosage forms include, but are not limited to, diluents, binders, lubricants, surfactants, coloring agents, flavors, buffering agents, preservatives, stabilizing agents and the like.

Diluents, also termed "fillers" include, for example, dicalcium phosphate dihydrate, calcium sulfate, lactose, cellulose, kaolin; mannitol, sodium chloride, dry starch, hydrolyzed starches, silicon dioxide, colloidal silica, titanium oxide, alumina, talc, microcrystalline cellulose, and powdered sugar. For administration in liquid form, the diluents include, for example, ethanol, sorbitol, glycerol, water and the like.

Binders are used to impart cohesive qualities to the formulation. Suitable binder materials include, but are not limited to, starch (including corn starch and pregelatinzed starch), gelatin, sugars (including sucrose, glucose, dextrose, lactose and sorbitol), polyethylene glycol, waxes, natural and synthetic gums, e.g., acacia, tragacanth, sodium alginate, celluloses, and Veegum, and synthetic polymers such as polymethacrylates and polyvinylpyrrolidone.

Lubricants are used to facilitate manufacture; examples of suitable lubricants include, for example, magnesium stearate, calcium stearate, stearic acid, glyceryl behenate, and polyethylene glycol.

Surfactants may be anionic, cationic, amphoteric or nonionic surface active agents, with anionic surfactants preferred. Suitable anionic surfactants include, but are not limited to, those containing carboxylate, sulfonate and sulfate ions, associated with cations such as sodium, potassium and ammonium ions. Particularly preferred surfactants include, but are not limited to: long alkyl chain sulfonates and alkyl aryl sulfonates such as sodium dodecylbenzene sulfonate; dialkyl sodium sulfosuccinates, such as sodium bis-(2-ethylhexyl)-sulfosuccinate; and alkyl sulfates such as sodium lauryl sulfate.

Stabilizing agents such as antioxidants, include, but are not limited to, propyl gallate, sodium ascorbate, citric acid, calcium metabisulphite, hydroquinone, and 7-hydroxycoumarin.

If desired, the present compositions may also contain minor amounts of nontoxic auxiliary substances such as wetting or emulsifying agents, preservatives, and the like.

As mentioned, any of the compositions of the invention may be used alone or in combination with one or more additional therapeutic agents, for the treatment of the disease from which the treated subject suffers. The amount of both the compound and the additional therapeutic agent that may be combined with the carrier materials to produce a composition or delivery system will vary depending upon the host treated and the particular mode of administration. In some embodiments, the compositions of this invention should be formulated so that a dosage of between 0.01-1 g/kg body weight/day of trehalose can be administered. The dose of the trehalose depends on the condition and the illness of the patient, and the desired daily dose. In human therapy, the daily dose can be 10-3000 mg, for example, 10, 15, 20, 30, 40, 50, 75, 100, 200, 300, 400, 500, 600 700, 800, 900 or 1000 mg. These amounts are administered in doses which can be divided into 2-3 smaller doses for each day.

In certain embodiments, the active ingredients in the present compositions and delivery systems can act synergistically in combination with each other and can further act synergistically in the presence of an additional therapeutic agent. Therefore, the amount of compound(s) and additional therapeutic agent(s) in such compositions will be less than that required in a monotherapy utilizing only that therapeutic agent.

Toxicity and therapeutic efficacy of the formulations described herein can be determined by standard pharmaceutical procedures in cell cultures or experimental animals, e.g., procedures used for determining the maximum tolerated dose (MTD), the $ED_{50}$, which is the effective close to achieve 50% of maximal response, and the therapeutic index (TI), which is the ratio of the MTD to the $ED_{50}$. Obviously, formulations with high TIs are the most preferred formulations herein, and preferred dosage regimens are those that maintain plasma levels of the trehalose at or above a minimum concentration to maintain the desired therapeutic effect. Dosage will, of course, also depend on a number factors, the site of intended delivery, the route of administration, and other pertinent factors known to the prescribing physician.

As indicated above, trehalose or any of the formulations comprising thereof as herein defined may be used alone or in combination with one or more additional therapeutic agents for the treatment of the diseases from which the treated subjects suffer. The amount of both the compound and the additional therapeutic agent that may be combined with trehalose or any of the formulations comprising thereof as herein defined will vary upon the subject treated and the particular diseases and mode of administration.

In certain embodiments, the active ingredients in the present compositions and delivery systems can act synergistically in combination with each other and can further act synergistically in the presence of an additional therapeutic agent. Therefore, the amount of compound(s) and additional therapeutic agent(s) in such compositions will be less than that required in a monotherapy utilizing only that therapeutic agent.

In another one of its aspects the presently disclosed subject matter provides Trehalose or a pharmaceutical formulation comprising same, for use in a method for treating or alleviating a disease associated with abnormal protein aggregation and/or inclusion bodies formation in myocytes, neurons and other cells or extracellular compartments or at least one symptom associated therewith, in a human subject in need thereof, said method comprising parenterally administering to said subject a therapeutically effective amount of trehalose or a pharmaceutical formulation comprising the same.

In yet another one of its aspects the presently disclosed subject matter provides an aqueous pharmaceutical formulation comprising a therapeutically effective amount of trehalose as a sole active ingredient, wherein the formulation has a pH about 4.5 to 7.0 and contains less than 0.74 endotoxin units per ml and wherein said pharmaceutical formulation is adapted for parenteral administration.

In some embodiments the aqueous pharmaceutical formulation as herein defined may be adapted for intravenous, intramuscular or intraperitoneal administration.

In other embodiments the aqueous pharmaceutical formulation as herein defined is adapted for intravenous, intramuscular or intraperitoneal administration.

As indicated above the aqueous pharmaceutical formulation as herein defined optionally further comprises at least one pharmaceutically acceptable additive, carrier, excipient or diluents.

In further embodiments the aqueous pharmaceutical formulation as herein defined is wherein the concentration of the trehalose is between about 0:1% (w/v) to about 50% (w/v). In further specific embodiments the aqueous pharmaceutical formulation as herein defined is wherein the concentration of the trehalose is about 10% (w/v).

In some embodiments the aqueous pharmaceutical formulation as herein defined is wherein the formulation has an osmolality of about 280-330 mOsm/kg.

In other embodiments the aqueous pharmaceutical formulation as herein defined is wherein the formulation is administered at a frequency between once daily to once per month.

The aqueous pharmaceutical formulation, as herein defined may be where said therapeutically effective amount of trehalose is from about 1 gram to about 100 gram for each daily injection and no more than about 1 gram/kg body weight of said subject per day.

In other embodiments the aqueous pharmaceutical formulation as herein defined is wherein the formulation is administered once daily at from about 10 mg/kg/day to about 1 gram/kg/day of trehalose.

In still further embodiments the aqueous pharmaceutical formulation as herein defined is wherein the formulation is administered at a frequency of between once daily to once per month at a dose of about 5 to about 35 grams of trehalose.

In further specific embodiments the aqueous pharmaceutical formulation as herein defined is for administration once daily, once every other day, twice a week, once a week, once every two weeks, once every three weeks or once a month.

In still further specific embodiments the aqueous pharmaceutical formulation as herein defined is wherein the dose is 5, 8, 15, 30, 40 or 50 grams.

In yet further embodiments the aqueous pharmaceutical formulation as herein defined is wherein the rate of administration is such that the maximum endotoxin level is less than 5 endotoxin units per kilogram of body weight per hour.

The aqueous pharmaceutical formulation of the presently disclosed subject matter may be where the formulation is adapted for intravenous administration and wherein said administration is completed within from about 75 to about 120 minutes, specifically within less than 90 minutes.

In some embodiments the aqueous pharmaceutical formulation as herein defined is for treating a disease associated with abnormal protein aggregation and/or inclusion bodies formation in myocytes, neurons and other cells or extracellular compartments or for alleviating a sign or symptom associated therewith in a human subject in need thereof.

The presently disclosed subject matter further provides a kit comprising:
(a) pharmaceutically acceptable trehalose or active derivative thereof;
(b) at least one pharmaceutically acceptable additive, carrier, excipient and diluent;
(c) means for preparing an injectable aqueous solution of the trehalose by mixing said trehalose with at least one of said additive, carrier, excipient and diluent;

(d) means for parenterally administering said injectable solution to a patient in need;
(d) instructions for use.

Injectable aqueous solution of the trehalose may be prepared by any method well known in the art, for example as recited herein in the accompanying Examples. Parenterally administering the injectable solution as herein defined well known in the art of the skilled physician.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

The invention will be further described in the following examples, which do not limit the scope of the invention described in the claims.

Various embodiments and aspects Of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative, of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Example 1 Trehalose

Trehalose, dihydrate was obtained from two different commercial sources (Hayashibara and Pfanstiehl). The samples were kept at room temperature until analysis, and were analyzed by accepted methods to verify specifics. The results are presented in Table 1 below.

TABLE 1

Analysis of trehalose dihydrate

| Test | Required Specifications | Sample Pfanstiehl |
|---|---|---|
| Assay | 97.0-102.0% w/w on anhydrous basis | 99.4% (conforms) |
| Related substances | Maltotriose ≤0.5% w/w | Conforms |
| | Any peak eluting before trehalose ≤0.5% w/w | Conforms |
| | Glucose ≤0.5% w/w | Conforms |
| | Any peak eluting after trehalose ≤0.5% w/w | Conforms |

As shown in Table 1 above, the tested trehalose dihydrate preparations conform with the accepted practice concerning use of trehalose in pharmaceutical compositions, namely comprise 97.0-102.0% w/w active ingredient (trehalose), with any peak eluting before trehalose at a concentration of less than 0.5% w/w, glucose at less than 0.5% w/w and with any peak eluting after trehalose at less than 0.5% w/w.

The trehalose used was commercially available trehalose dihydrate, comprising 97.0-102.0% w/w active ingredient (trehalose), with glucose at less than 0.5% w/w and other contaminants at less than 1%.

Example 2 Preparation of Trehalose Solution for IV Injection

A formulation comprising trehalose was prepared under sterile conditions by dissolving trehalose dihydrate in water and the resulting clear and colorless liquid was analyzed to identify any impurities or contaminants.

TABLE 2

Analysis of trehalose formulation

| Test | Specification | Result |
|---|---|---|
| Appearance of container ATP007 | Clear glass 30R vial with grey rubber stopper, aluminium seal and white flip off lid | Clear glass 30R vial with grey rubber stopper, aluminium seal and white flip off lid. |
| Appearance of contents ATP007 | Clear colourless liquid essentially free from visible particulate matter | Clear colourless liquid essentially free from visible particulate matter |
| P537 Identity ATP1323 | Retention time of the P537 peak ± 5% of standard | Retention time of the P537 peak is within ± 5% of the P537 standard peak |
| P537 Content Assay ATP1323 | 90.0% to 110.0% label claim | 99.8% |

TABLE 2-continued

Analysis of trehalose formulation

| Test | Specification | Result |
|---|---|---|
| P537 Related Substances (% label claim) ATP1323 | Report individual impurities ≥0.05% label claim Report total impurities Maltotriose and other polysaccharides eluting before P537: ≤0.5% Glucose and peaks eluting after P537 ≤0.5% Total impurities 2.0% | Maltotriose: None detected Unknown RRT0.90: 0.1% Glucose: None detected Total Impurities: 0.1%. |
| pH ATP164 | 4.5 to 7.0 | 6.2 |
| Osmolality ATP841 | 280-330 mOsm/kg | 289 mOsm/kg |
| Particulate matter USP <788>, Ph. Eur 2.9.19 | Particulates ≥10 μm: NMT 6000 Particulates ≥25 μm: NMT 600 | ≥10 μm: 7 ≥25 μm: 0 |
| Extractable Volume USP <1>, Ph. Eur 2.9.17 | Not less than 30 ml | 32 ml |
| Endotoxins USP <85>, Ph. Eur 2.6.14 | <0.24 EU/ml | Point 1 tray 1: <0.1 EU/ml Point 4 tray 31: <0.1 EU/ml Point 8 tray 72: <0.1 EU/ml |
| Sterility USP <71>, Ph. Eur 2.6.1 | Complies | No growth |

The formulation was sterile and comprised 10% trehalose, with total impurities at a concentration of 0.1%, pH of 6.2 and an osmolality of 289 mOsm/kg and endotoxins at less than 0.1. EU/ml.

Example 3 Preclinical Pharmacokinetic Studies

The plasma and muscle concentrations of trehalose in male Sprague-Dawley (SD) rats was determined after intravenous bolus (IV) and oral gavage (PO) administration.

All applicable portions of the study confirmed to the following regulations, and guidelines regarding animal care and welfare: AAALAC International and NIH guidelines as reported in the "Guide for the Care and Use of Laboratory Animals;" National. Research Council ILAR, Revised 1996.

The study included 42 SD rats (male, 250 to 350 grams in weight, the Shanghai SLAC Laboratory Animal Co. Ltd.). Animals were administered with a volume of 5 ml/kg trehalose formulation (trehalose dihydrate in sterilized, water at 200 mg/mL) to achieve a nominal dose of 1 gr/kg, intravenously or orally.

Blood samples were collected after each dose administration and processed for plasma. Muscle samples (hind leg muscle) were collected and homogenized. The concentrations of trehalose in plasma and muscle homogenate samples were analyzed by qualified bioanalytical LC/MS/MS methods.

Pharmacokinetics Data Analysis

Plasma concentration data of trehalose was subjected to a non compartmental pharmacokinetic analysis using Win-Nonlin software program (version 6.3, Pharsight, Mountain View, Calif.). Zero-time intercept concentration (C0), volume of distribution (Vdss), Clearance (Cl), peak plasma concentrations (Cmax) and the corresponding peak times (Tmax), terminal half-life (T½), mean residence time (MRT) from time zero to the last time point (MRT0-last), MRT from time zero to infinity (MRT0-inf), the area under the plasma concentration-time curve (AUC) from time zero to the last time point (AUC0-last) and AUC from time zero extrapolated to infinity (AUC0-inf) were calculated using the linear/log trapezoidal rule. Nominal sampling times were used, to calculate all pharmacokinetic parameters since there was not any deviation larger than 5% between the actual and nominal sampling times.

The values of muscle to plasma concentration and AUC ratio (M/P ratio) were both calculated.

Trehalose Concentration in Plasma and Muscle

Pharmacokinetic parameters of trehalose in the plasma and muscle following single intravenous or oral administration of trehalose dihydrate solution (200 mg trehalose dihydrate per 1 mL sterilized water) at 1000 mg/kg to male SD rats are presented in Table 3 below.

Figure 1:
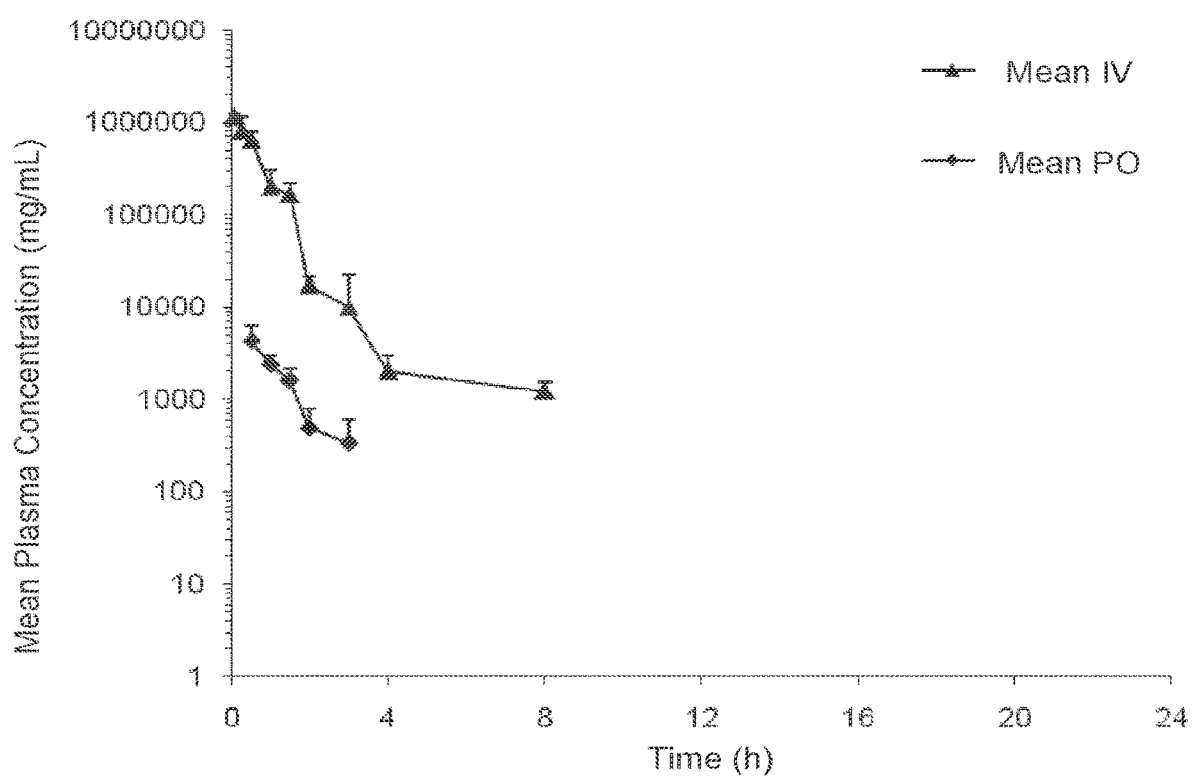
FIG. 1 Mean plasma concentration of trehalose after i.v. or p.o. administration.

Individual and mean plasma concentrations of trehalose following intravenous or oral administration of trehalose dihydrate solution (200 mg trehalose dihydrate per 1 mL sterilized water) at 1000 mg/kg to male SD rats are presented in Table 3 and shown graphically in FIG. 1.

Individual and mean muscle concentrations of trehalose following single intravenous or oral administration of trehalose dihydrate solution (209 mg trehalose dihydrate per 1 mL sterilized water) at 1000 mg/kg to male SD rats are presented in Table 3 as well. Plasma and muscle concentrations comparison for trehalose following single intravenous or oral administration of trehalose dihydrate at 1000 mg/kg to male SD rats are nd shown graphically in FIGS. 2 to 3.

Following a single intravenous dose of trehalose solution (200 mg trehalose dihydrate per 1 mL sterilized water) at 1000 mg/kg to male fasted SD rats in tested groups 1 to 5, trehalose showed a total clearance (Cl) of 17.2 mL/min/kg (approximately 31.3% of rat liver blood flow (=55 mL/min/kg)), with the averaged elimination half life ($T_{1/2}$) of 2.07 hours. The $C_0$ was 1,370,000 ng/mL.

The volume distribution ($V_{dss}$) was at 0.685 L/kg. The mean plasma exposure $AUC_{0\text{-}last}$ (48 hr) was 778,000, ng·hr/mL.

With an oral administration of trehalose dihydrate solution (200 mg trehalose dihydrate per 1 mL sterilized water) to male SD rats in tested groups 6 to 10, trehalose maximum plasma concentration ($C_{max}$=4,280, ng/mL) was attained at 0.5 hour post dose ($T_{max}$). The $AUC_{0\text{-}last}$ (3 hr) was 4,520 ng/mL·hr. The absolute bioavailability of trehalose was estimated tote as low as 0.601%.

The pharmacokinetic properties of trehalose demonstrated a rapid absorption with a time to reach peak plasma concentrations, but the absolute oral bioavailability was very low, which noted that the compound may undergo a significant presystemic-metabolism.

Following a single intravenous dose of trehalose dihydrate solution (200 mg trehalose dihydrate per 1 mL sterilized water) at 1000 mg/kg to male SD rats in tested groups 1 to 5, the $C_{max}$ of trehalose in muscle was 3730 ng/mL, which was observed at 8 hours ($T_{max}$) post dose. The muscle exposure $AUC_{0\text{-}last}$ (48 hr) was 107,000 ng·hr/mL with the elimination half life 33.8 hours. The PK parameters of muscle samples in drug treated oral group (Groups 6 to 10) could not be calculated because they were below LLOQ The mean ratios of muscle trehalose concentration to plasma concentration ranged froth 2.88 to 3.76 in male SD rats following intravenous administration. Muscle to plasma concentration ratios for trehalose upon oral administration were below LLOQ and not calculable.

CONCLUSIONS

Following intravenous or oral administrations of trehalose dihydrate solution in sterilized water at 1000 mg/kg to male SD rats, trehalose in plasma and muscle tissue were determined. Plasma glucose was also monitored for each sample from study animals of drug treated groups. The following conclusions can be made:

First, following IV administration, the total clearance (Cl) of trehalose was 17.2 mL/min/kg, accounting for approximately 3.1.3% of liver blood flow, a moderate value of hepatic extraction ratio. The $V_{dss}$ and $T_{1/2}$ were 0.685 L/kg, and 2.07 hours respectively. The mean plasma exposure $AUC_{0\text{-}last}$ was 778,000 ng·hr/mL.

Following oral administration, trehalose demonstrated a rapid absorption with $T_{max}$ observed at 0.50 hours post dose, but the absolute oral bioavailability was as low as 0.601%, suggesting presystemic metabolism may play an important role. $T_{1/2}$ of trehalose was markedly shortened in oral administration rats in comparison to the intravenous group.

Following IV administration, the mean ratios of muscle trehalose concentration to plasma concentration, ranged from 2.88 to 3.76 in male SD rats.

Finally, it was observed that trehalose dihydrate was well tolerated by the rats at the given dosage.

TABLE 3

Pharmacokinetic parameters

| | Plasma | | Muscle | |
|---|---|---|---|---|
| Group ID | IV | PO | IV | PO |
| $C_0$ (ng/mL) | 1370000 | — | — | ND |
| $C_{max}$ (ng/mL or ng/g) | — | 4280 | 3730 | ND |
| $T_{max}$ (h) | — | 0.500 | 8.00 | ND |
| $T_{1/2}$ (h) | 2.07 | 0.740 | 33.8 | ND |
| CI (mL/min/kg) | 17.2 | — | — | ND |
| $V_{dss}$ (L/kg) | 0.685 | — | — | ND |
| $AUC_{0\text{-}last}$ (ng · h/mL or ng · h/g) | 778000 | 4520 | 107000 | ND |
| $AUC_{0\text{-}inf}$ (ng · h/mL or ng · h/g) | 781000 | 4870 | 183000 | ND |
| $MRT_{0\text{-}last}$ (h) | 0.618 | 1.04 | 21.1 | ND |

TABLE 3-continued

Pharmacokinetic parameters

| | Plasma | | Muscle | |
|---|---|---|---|---|
| Group ID | IV | PO | IV | PO |
| $MRT_{0\text{-}inf}$ (h) | 0.666 | 1.26 | 52.6 | ND |
| $AUC_{0\text{-}inf}/AUC_{0\text{-}last}$ (%) | 100 | 108 | 171 | ND |
| [c]Bioavailability (%) | — | 0.601 | — | — |
| [d]AUC ratio | — | — | 0.234 | ND |

Abbreviations:
ND = Not determined;
[c]Bioavailability (%) was calculated with mean $AUC_{0\text{-}inf}$ and norminal dose;
[d]AUC Ratio = Muscle $AUC_{0\text{-}inf}$/Plasma $AUC_{0\text{-}inf}$; $AUC_{(0\text{-}inf)}$ >120% of $AUC_{(0\text{-}last)}$.

Thus, as demonstrated in Table 3, the trehalose in the IV administered formulation showed $T_{1/2}$ of 2.07 hour in plasmas, over two-fold higher than the plasma $T_{1/2}$ obtained for trehalose in the orally administered formulation (0.740 hours). In addition, the muscle $T_{1/2}$ obtained for the trehalose in the IV administered formulation was 33.8 hours. The AUC values obtained for plasma and muscle when the formulation was administered IV were also significantly higher than the respective AUC values of formulation administered orally.

In addition, as demonstrated in FIG. 1, the mean plasma concentration of the trehalose in the IV administered formulation is higher than the mean plasma concentration of the trehalose in the orally administered formulation at each of the tested, time points.

Interestingly, FIG. 2, which demonstrates plasma versus muscle concentrations of trehalose for a trehalose formulation administered intravenously, shows, that muscle concentrations am higher than plasma concentrations of trehalose. Plasma and muscle concentrations of trehalose were undetectable for a trehalose formulation administered orally.

Example 4 Determination of Endotoxin Level

It is accepted that the maximal allowed level of endotoxin in formulations administered intravenously is 5 endotoxin units (EU) per kg body Mass per hour (5 EU/kg/hr). In order to determine the theoretical maximum endotoxin level IV per kg body mass/hour (K) in trehalose formulation (solution of trehalose dihydrate in sterilized water), the following calculations were made:

TABLE 4

Calculation of maximal endotoxin levels in trehalose formulations

| Endotoxin contribution | 15 gr trehalose formulation | 30 gr trehalose formulation |
|---|---|---|
| 2.4 EU/gr (trehalose) | 36 | 72 |
| 0.5 EU/ml (solvent) | 75 (in 150 ml) | 150 (in 300 ml) |
| Total EU in formulation | 111 | 222 |
| Assuming 75 min infusion | 88.8 EU/hr | 177.6 EU/hr |
| K for 60 kg body weight | 1.5 | 3.0 |
| K for 50 kg body weight | 1.8 | 3.6 |
| K for 40 kg body weight | 2.2 | 4.4 |

As indicated in Table 4 above, endotoxin level per ml in trehalose formulations prepared with standard solvents (e.g. water, saline, etc.), is 0.74 EU/ml. Assuming a moderate infusion rate of 75 minutes, for a body weight of 60, 50 and 40 kg the endotoxin level in trehalose 10% (w/v) formulations is 1.5, 1.8 and 2.2 EU/kg/hr, respectively, for a formulation comprising 15 gr trehalose and 3.0, 3.6 and 4.4 EU/kg/hr, respectively, for a formulation comprising 30 gr trehalose.

Accordingly, under the maximum rate planned, the endotoxin level for a body weight of 60, 50 and 40 kg will be 2, 2.4 and 3 EU/kg/hr, respectively, for a formulation comprising 15 gr trehalose (in 150 ml solvent) and 4, 4.8 and 6 EU/kg/hr, respectively, for a formulation comprising 30 gr trehalose (in 300 ml solvent).

Example 5 Safety Studies

The safety and tolerability of trehalose has been extensively investigated, as detailed below. Trehalose median lethal dose ($LD_{50}$) was examined in mice, rats and dogs. Neither species showed any signs of toxicity and no deaths occurred after oral and intravenous administration. The results are summarized in Table 5 below:

TABLE 5

LD50 of trehalose in animals

| SPECIES | ROUTE | LD50 (mg/kg bw) |
|---|---|---|
| Mouse | Oral | >5000 |
| Mouse | Intravenous | >1000 |
| Rat | Oral | >16000 |
| Rat | Oral | >5000 |
| Rat | Intravenous | >1000 |
| Dog | Oral | >5000 |
| Dog | Intravenous | >1000 |

In addition, trehalose is recognized as a safe food ingredient as well as a GRAS material used in the pharmaceutical industry as an excipient for oral, intraocular and IV drug formulations. In several studies, healthy volunteers were given oral doses of trehalose ranging from 10 to 60 gr. Apart from mild abdominal symptoms (e.g. flatulence, distension, borborygmus and occasional diarrhea) no other safety issues were reported [18].

Trehalose has been used as a protein stabilizer in several commercially available protein drugs for over a decade and its safety has repeatedly been established in patient populations at advanced stages of malignant diseases, hemophilia and related clotting disorders. These drugs are approved for use for, several years, and are sometimes given to patients as frequently as every 8 hours through 2-3 weeks intervals.

Example 6 Treatment of OPMD Patients with Trehalose

The potential benefit of trehalose in ameliorating the symptoms of OPMD or slowing the deterioration of OPMD patients, is currently examined in a clinical study in human patients.

The study is a randomized, double-blind, dose escalation and parallel-group dose-controlled study of treatment of patients with Oculopharyngeal Muscular Dystrophy (OPMD) IV with trehalose aqueous injectable solution is carried out in three medical centers.

Exploratory Phase

Screening Period (Week-4/Day-28 to Week 0/Day 0)

Screening assessments are conducted over two visits within 28 days prior to the start of therapy, as specified in the Schedule of Assessments.

Treatment Period 1 (Week 1 to Week 24)

All eligible patients receive study treatment once a week. Initially, all eligible patients receive intravenously one dose of trehalose (8 g) in a 10% (w/v) injectable aqueous solution per week (80 ml solution). This is followed by intravenous administration Of a further single trehalose dose (15 g) in a 10% (W/v) injectable aqueous solution during the following week. Following determination of safety, at the next visit on subsequent week, patients are randomized at a 1:1 ratio (double-blind) to receive either 15 g or 30 g of trehalose (in an aqueous 10% (w/v) solution) for 24 weeks. The first 4 infusions are done at the clinic under professional direction. Patients return to the clinic once a month for drug infusion and study assessments, as indicated in the Schedule of Procedures; all other weekly infusions May be done in the patient's home or in the clinic.

Pivotal Phase

Treatment Period 2 (Week 25 to Week 72)

Patients continue weekly IV infusions of trehalose aqueous injectable solution.

Follow-Up Period (4 Weeks Post-Dose)

Patients are seen at a post-treatment follow-up visit, 4 weeks after the final dose of $24^{th}$ week.

Study Population

Up to 15 adult patients with OPMD are enrolled into the study at each of the three study centers. A minimum of 42 patients are enrolled in total. A control group receiving no treatment may be added.

Inclusion Criteria

1. Males and females
2. 18-80 years (inclusive) of age
3. Genetically diagnosed with OPMD
4. Moderate dysphagia (abnormal drinking test at screening and on the first dosing day, before drug administration)
5. Patients must be ambulatory; and capable of performing the muscle functional and strength assessments
6. Patients who provide written informed consent to participate in the study
7. Body Mass Index (BMI) <30 kg/m²
8. Female patients of child-bearing potential must have a negative serum pregnancy test at screening
9. Male and females must agree to use acceptable birth control Exclusion Criteria 1. Diabetes mellitus Type 1 or 2
2. Other major diseases, e.g. renal failure (creatinine clearance <60 ml/min), liver failure and chronic liver diseases (e.g. hepatitis B or C), HIV carriers, tuberculosis, SLE, rheumatoid polyarthritis, sarcoidosis, collagenosis.

3. Uncontrolled heart disease, e.g., CHF.
4. Other neuromuscular diseases.
5. Other disorders associated with esophageal dysphagia: e.g. gastroesophageal reflux (GERD), esophageal stricture due to mechanical or chemical trauma, infection (e.g. esophageal moniliasis), drug-induced dysphagia (e.g. bisphosphonates), esophageal rings and webs, spastic motility disorders of the esophagus.
6. History of malignancy.
7. History of neck irradiation.
8. Pregnant or currently lactating women.
9. Obesity (BMI≥30) and associated morbidity.
10. Prior pharyngeal myotomy.
11. Weight loss of more than 10% in the last 12 months.
12. Known hypersensitivity to any ingredients in the injection.

Investigational Product Route and Dosage Form

A 10% (w/v) IV solution of trehalose is administered in a single injection, once a week for 72 weeks. The solution is delivered over approximately from about 70 to about 120 minutes.

Initial dose per injection in Week 1 is 8 g trehalose, Second week dose is 15 g, and dose at weeks 3 to week 72 is 15 or 30 g.

Safety and Tolerability

The primary safety endpoint is the frequency, severity, and duration of adverse events (AEs), including clinically significant laboratory abnormalities after administration of the trehalose injectable solution.

Safety is evaluated on the basis of AEs and concomitant medications; physical examination; vital signs (prior to, every 30 minutes during, and 30 minutes following administration). Test include complete blood count (CBC) with differential, electrolytes (Na, K, Cl), BUN, creatinine, glucose, liver function tests (ALT, AST, total bilirubin, direct bilirubin, alkaline phosphatase, and serum albumin), and dipstick urinalysis.

Efficacy Outcomes/Disease Markers Evaluation

The following disease markers are assessed at specified times:
Penetration Aspiration Score (using Videofluoroscopy)
SWAL-QOL
Muscle timed functional and strength assessments
Changes compared to baseline will be measured for each patient, and the total change in scores for the treatment groups in each pre-determined efficacy endpoint is statistically analyzed.

Additional assessments may be of weight and drinking.
Percutaneous Core Needle Biopsy (PCNB) is performed to obtain muscle fiber for histology.

Pharmacokinetics

The pharmacokinetic of trehalose are assessed in patients at the dose of 15 g or 30 g trehalose. Trehalose blood concentration is measured pre-dose (up to 60 minutes before drug administration); and every 30 minutes after dosing is initiated, for 5 hours or until glucose levels return to normal, whichever occurs first.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for ameliorating a symptom in a subject wherein the subject has a disorder selected from: spinocerebellar ataxia (SCA) associated with a polyglutamine repeat mutation, spinal and bulbar muscular atrophy (SBMA), dentatomral-pailidoluyssan atrophy (DRPLA), Pick's disease, corticobasal degeneration (CBD), progressive supranuclear palsy (PSP), and frontotemporal dementia;
wherein the method comprises parenterally administering to said subject a pharmaceutical formulation comprising trehalose as the sole active ingredient;
wherein the concentration of trehalose in said formulation is between about 0.1% (w/v) to about 50% (w/v); and
wherein the administration is completed within less than 120 minutes.

2. The method of claim 1, wherein said pharmaceutical formulation is an injectable solution for parenteral administration.

3. The method of claim 1, wherein said pharmaceutical formulation further comprises at least one pharmaceutically acceptable additive, carrier, excipient, or diluent.

4. The method of claim 1, wherein said parenteral administration is any one of intravenous, intramuscular, or intraperitoneal administration.

5. The method of claim 1, wherein the pharmaceutical formulation has a pH about 4.5 to 7.0.

6. The method of claim 1, wherein the pharmaceutical formulation contains less than 0.75 endotoxin units per mL.

7. The method of claim 1, wherein the pharmaceutical formulation is administered to the subject at a per administration dose of about 10 to about 1000 mg/kg subject body weight.

8. The method of claim 7, wherein the pharmaceutical formulation is administered to the subject at a per administration dose of about 30 to about 100 mg/kg subject body weight.

9. The method of claim 7, wherein the formulation is administered to the subject at a per administration dose of about 100 to about 300 mg/kg subject body weight.

10. The method of claim 7, wherein the pharmaceutical formulation is administered to the subject at a per administration dose of about 100 to about 150 mg/kg subject body weight.

11. The method of claim 7, wherein the pharmaceutical formulation is administered to the subject at a per administration dose of about 200 to about 600 mg/kg subject body weight.

12. The method of claim 1, wherein the pharmaceutical formulation further comprises a trehalase inhibitor.

13. The method of claim 1, wherein the pharmaceutical formulation is administered to the subject daily.

14. The method of claim 1, wherein the pharmaceutical formulation is administered to the subject twice per day.

* * * * *

UNITED STATES PATENT AND TRADEMARK OFFICE
CERTIFICATE OF CORRECTION

Page 1 of 1

PATENT NO. : 10,869,831 B2
APPLICATION NO. : 16/460046
DATED : December 22, 2020
INVENTOR(S) : Megiddo It is certified that error appears in the above-identified patent and that said Letters Patent is hereby corrected as shown below:

On the Title Page

Column 2 (item (56) other publications), Line 5, please delete "Stroike," and insert -- Stroke, --, therefor.

In the Claims

Column 32, Line 14 (approx.), in Claim 1, delete "dentatomral-pailidoluyssan" and insert -- dentoral-pallidoluysian --, therefor.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*